(12) United States Patent
Ray et al.

(10) Patent No.: US 12,213,811 B2
(45) Date of Patent: *Feb. 4, 2025

(54) SYSTEMS, DEVICES, AND METHODS FOR DEVELOPING A MODEL FOR USE WHEN PERFORMING OXIMETRY AND/OR PULSE OXIMETRY AND SYSTEMS, DEVICES, AND METHODS FOR USING A FETAL OXIMETRY MODEL TO DETERMINE A FETAL OXIMETRY VALUE

(71) Applicant: Raydiant Oximetry, Inc., San Ramon, CA (US)

(72) Inventors: Neil Padharia Ray, Sacramento, CA (US); Jana M Kainerstorfer, Pittsburg, PA (US); Adam Jacobs, Hollis, NH (US); Andrew Prescott, Bedford, NH (US)

(73) Assignee: Raydiant Oximetry, Inc., San Ramon, CA (US)

( * ) Notice: Subject to any disclaimer, the term of this patent is extended or adjusted under 35 U.S.C. 154(b) by 72 days.

This patent is subject to a terminal disclaimer.

(21) Appl. No.: 18/106,486

(22) Filed: Feb. 7, 2023

(65) Prior Publication Data
US 2023/0172565 A1  Jun. 8, 2023

Related U.S. Application Data

(63) Continuation of application No. 17/804,555, filed on May 27, 2022, now Pat. No. 11,596,361, which is a
(Continued)

(51) Int. Cl.
*A61B 5/00* (2006.01)
*A61B 5/1455* (2006.01)
*A61B 5/1464* (2006.01)

(52) U.S. Cl.
CPC ........ *A61B 5/7275* (2013.01); *A61B 5/14551* (2013.01); *A61B 5/1464* (2013.01);
(Continued)

(58) Field of Classification Search
None
See application file for complete search history.

(56) References Cited

U.S. PATENT DOCUMENTS

| 4,911,167 A | 3/1990 | Corenman et al. |
| 5,348,002 A | 9/1994 | Caro |

(Continued)

FOREIGN PATENT DOCUMENTS

| CN | 103381094 A | 11/2013 |
| CN | 209629664 U | 11/2019 |

(Continued)

OTHER PUBLICATIONS

Delpy, et al., "Quantification in tissue near-infrared spectroscopy," Phil. Trans. R. Soc. Lond. B, 352: 649-659, 1997.
(Continued)

*Primary Examiner* — Jay B Shah
(74) *Attorney, Agent, or Firm* — Resonance IP Law, PC

(57) ABSTRACT

A plurality of sets of simulated optical inputs that is simulated to travel through an animal model of tissue, thereby generating simulated light transmission data, and corresponding oximetry vales may be used to train a simulated fetal oximetry model to predict, or calculate, oximetry values for subsequently received sets of simulated light transmission data. The simulated fetal oximetry model may be adapted to train an in vivo fetal oximetry model that may be configured to predict, or calculate, fetal oximetry values for subsequently received sets of light transmission data received from an in vivo study of a pregnant mammal and her fetus.

21 Claims, 13 Drawing Sheets

Related U.S. Application Data continuation of application No. PCT/US2021/052092, filed on Sep. 24, 2021.

(60) Provisional application No. 63/083,064, filed on Sep. 24, 2020.

(52) U.S. Cl.
CPC .......... *A61B 5/7267* (2013.01); *A61B 5/7278* (2013.01); *A61B 5/742* (2013.01); *A61B 5/746* (2013.01)

(56) References Cited

U.S. PATENT DOCUMENTS

| | | |
|---|---|---|
| 5,524,617 A | 6/1996 | Mannheimer |
| 5,807,271 A | 9/1998 | Tayebi et al. |
| 5,835,558 A | 11/1998 | Maschke |
| 6,453,183 B1 | 9/2002 | Walker |
| 6,498,942 B1 | 12/2002 | Esenaliev et al. |
| 6,690,958 B1 | 2/2004 | Walker et al. |
| 7,047,055 B2 | 5/2006 | Boas et al. |
| 7,469,158 B2 | 12/2008 | Cutler et al. |
| 7,515,948 B1 | 4/2009 | Balberg et al. |
| 8,275,436 B2 | 9/2012 | Wang et al. |
| 8,644,900 B2 | 2/2014 | Balberg et al. |
| 9,757,058 B2 | 9/2017 | Ray |
| 9,968,286 B2 | 5/2018 | Ray |
| 10,362,974 B2 | 7/2019 | Ray |
| 11,116,412 B2 | 9/2021 | Ghiasi et al. |
| 2003/0073910 A1 | 4/2003 | Chance |
| 2004/0116789 A1 | 6/2004 | Boas et al. |
| 2006/0122475 A1 | 6/2006 | Balberg et al. |
| 2008/0208009 A1 | 8/2008 | Shklarski |
| 2009/0281402 A1 | 11/2009 | Chance |
| 2010/0081901 A1 | 4/2010 | Buice et al. |
| 2011/0218413 A1 | 9/2011 | Wang et al. |
| 2012/0184830 A1 | 7/2012 | Balberg et al. |
| 2012/0190946 A1 | 7/2012 | Bernreuter |
| 2013/0338460 A1 | 12/2013 | He et al. |
| 2015/0099950 A1 | 4/2015 | Al-Ali et al. |
| 2016/0015304 A1 | 1/2016 | Esenaliev et al. |
| 2016/0128594 A1 | 5/2016 | Amir et al. |
| 2017/0188920 A1 | 7/2017 | Ray |
| 2018/0070871 A1 | 3/2018 | Ray |
| 2019/0343437 A1 | 11/2019 | Ray |
| 2020/0022637 A1 | 1/2020 | Kurzrock et al. |
| 2020/0214603 A1 | 7/2020 | Ghiasi et al. |
| 2020/0245879 A1 | 8/2020 | Ghiasi et al. |

FOREIGN PATENT DOCUMENTS

| | | |
|---|---|---|
| EP | 1054620 B1 | 1/2010 |
| WO | 2004086966 A1 | 10/2004 |
| WO | 2009032168 A1 | 3/2009 |
| WO | 2018094391 A3 | 7/2018 |
| WO | 2018175100 A1 | 9/2018 |

OTHER PUBLICATIONS

Dildy, "Fetal Pulse Oximetry," Clinical Obstetrics and Gynecology, 54(1): 66-73, Mar. 2011.
Dildy, et al., "Current status of the multicenter randomized clinical trial on fetal oxygen saturation monitoring in the United States," European Journal of Obstetrics & Gynecology and Reproductive Biology, 72, Suppl. 1, pp. S43-S50, 1997.
Dildy, et al., "Intrapartum fetal pulse oximetry: Fetal oxygen saturation trends during labor and relation to delivery outcome," Am. J. Obstet. Gynecol., 171(3): 679-684, Sep. 1994.
Dildy, et al., "Intrapartum fetal pulse oximetry: Past, present, and future," American Journal of Obstetrics & Gynecology, 175(1): 1-9, Jul. 1996.
Dildy, et al., "Management of prolonged decelerations," OBG Management, 7 pgs., Nov. 2006.
Dildy, et al., "Preliminary Experience with Intrapartum Fetal Pulse Oximetry in Humans," Obstetrics and Gynecology, 81(4): 630-635, Apr. 1993.
Diniz, In Adaptive Filtering Algorithms and Practical Implemetation, Springer, Third Edition, pp. 636, 2008.
Dong, et al., "Simultaneously Extracting Multiple Parameters Via Fitting One Single Autocorrelation Function Curve in Diffuse Correlation Spectroscopy," IEEE Transactions on Biomedical Engineering, 60(2): 361-368, Feb. 2013.
Donlon, et al., "MEG Visual Stimuli Software," MEG Setup Documentation, pp. 3.
Durduran, et al., "Diffuse correlation spectroscopy for non-invasive, micro-vascular cerebral bloodflow measurement," NeuroImage, 85: 51-63, 2014.
Durduran, et al., "Diffuse optics for tissue monitoring and tomography," Reports on Progress in Physics, 73, pp. 44, 2010.
East, et al., "A cost-effectiveness analysis of the intrapartum fetal pulse oximetry multicentre randomised controlled trial (the FOREMOST trial)," BJOG An International Journal of Obstetrics and Gynaecology, pp. 1080-1087, 2006.
East, et al., "Fetal oxygen saturation and uterine contractions during labor," Am J Perinatol, 15(6): 345-349, Jun. 1998 (Abstract Only).
East, et al., "Fetal oxygen saturation during maternal bearing down efforts in the second stage of labor," Am J. Perinatol, 15(2): 121-124, 1998 (Abstract Only).
East, et al., "Fetal Oxygen Saturation Monitoring in Labour: An Analysis of 118 Cases," Aust. and NZ Journal of Obstetrics and Gynaecology, 37(4): 397-401, 1997.
East, et al., "Fetal pulse oximetry for fetal assessment in labour (Review)," The Cochrane Collaboration, pp. 76, 2014.
East, et al., "Intrapartum fetal scalp lactate sampling for fetal assessment in the presence of a non-reassuring fetal heart rate trace (Review)," The Cochrane Database of Systematic Reviews 2015, Issue 5. Art. No. CD006174, pp. 39, 2015.
East, et al., "Intrapartum Oximetry of the Fetus," Anesthesia & Analgesia, 105(6), pp. S59-S65, Dec. 2007.
East, et al., "The effect of intrapartum fetal pulse oximetry, in the presence of a nonreassuring fetal heart rate pattern, on operative delivery rates: A multicenter, randomized, controlled trial (the FOREMOST trial)," American Journal of Obstetrics and Gynecology, 194, pp. 606.e1-606.e16, 2006.
East, et al., "Update on intrapartum fetal pulse oximetry," Aust NZ J Obstet Gynaecol, 42(2): 119-124, 2002.
Eden, et al., "Reengineering Electronic Fetal Monitoring Interpretation: Using the Fetal Reserve Index to Anticipate the Need for Emergent Operative Delivery," Reproductive Sciences, 25(4): 487-497, 2018.
Eden, et al., "The "Fetal Reserve Index": Re-Engineering the Interpretation and Responses to Fetal Heart Rate Patterns," Fetal Diagnosis and Therapy, 43: 90-104, Jun. 2017.
Emberson, et al., "Isolating the effects of surface vasculature in infant neuroimaging using short-distance optical channels: a combination of local and globaleffects," Neurophotonics, 3(3), pp. 031406-1-031406-12, Jul.-Sep. 2016.
Eunson, "The long-term health, social, and financial burden of hypoxic-ischaemic encephalopathy," Developmental Medicine & Child Neurology, 57 (Suppl. 3): 48-50, 2015.
Evans, et al., "Re-engineering the interpretation of electronic fetal monitoring to identify reversible risk for cerebral palsy: a case control series," The Journal of Maternal-Fetal & Neonatal Medicine, pp. 10, 2018.
Fabbri, et al., "Optical measurements of absorption changes in two-layered diffusive media," Physics in Medicine & Biology, 49: 1183-1201, Mar. 18, 2004.
Fantini, et al., "Frequency-domain multichannel optical detector for nonivasive tissue spectroscopy and oximetry," Optical Engineering, 34(1): 32-42, Jan. 1995.
Fantini, et al., "Frequency-domain techniques for tissue spectroscopy and imaging", In Handbook of Optical Biomedical Diagnostics, Second Edition, vol. 1: Light Tissue Interaction, Chapter 7, pp. 1-52, 2002.

(56) References Cited

OTHER PUBLICATIONS

Farrell, et al., "Influence of layered tissue architecture on estimates of tissue optical properties obtained from spatially resolved diffuse reflectometry," Applied Optics, 37(10): 1958-1972, Apr. 1, 1998.

Farzam, "Hybrid diffuse optics for monitoring of tissue hemodynamics with applications in oncology," Doctoral Thesis in Photonics, Institute of Photonic Sciences, pp. 240, Jul. 2014.

Fatemi, et al., "Hypoxic Ischemic Encephalopathy in the Term Infant," Author manuscript; available in PMC, Dec. 1, 2010, pp. 23, 2009.

Figures of Two-minute tracing showing fetal heart rate, and Pulse oximetry tracing from 25-week gestation fetus undergoing open congenital diaphragmatic hernia repair, Anesthesia for Fetal Procedures and Surgery, pp. 280-281.

Firbank, et al., "An investigation of light transport through scattering bodies with non-scattering regions," Phys. Med. Biol., 41: 767-783, 1996.

Fong, D.D., et al., "Contextually-aware Fetal Sensing in Transabdominal Fetal Pulse Oximetry," 2020 ACM/IEEE 11th International Conference on Cyber-Physical Systems (ICCPS), Apr. 2020.

Fong, D.D., et al., "Optode Design Space Exploration for Clinically-robust Non-invasive Fetal Oximetry," ACM Transactions on Embedded Computing Systems, vol. 18, No. 5s, Article 63, Oct. 2019.

Fong, et al., "Recovering the Fetal Signal in Transabdominal Fetal Pulse Oximetry," Smart Health, 9-10: 23-26, Jul. 9, 2018.

Fong, et al., "Transabdominal Fetal Blood Oximetry," Website of the University of California, Davis, Office of Research, http://research.ucdavis.edu/u/s/ia, pp. 1, 2017.

Fong, et al., "Transabdominal Fetal Pulse Oximetry: The Case of Fetal Signal Optimization," 2017 IEEE 19th International Conference on e-Health Networking, Applications and Services (Healthcom), pp. 6, 2017.

Franceschini, et al., "Assessment of Infant Brain Development with Frequency-Domain Near-Infrared Spectroscopy," Pediatr Res., 61(5): 546-551, 2007.

Franceschini, et al., "Influence of a superficial layer in the quantitative spectroscopic study of strongly scattering media," Applied Optics, 37(31): 7447-7458, Nov. 1, 1998.

Gagnon, et al., "Further improvement in reducing superficial contamination in NIRS using doubleshort separation measurements," NeuroImage, 85: 127-135, 2014.

Gagnon, et al., "Short separation channel location impacts the performance of short channel regression in NIRS," NeuroImage, 59: 2518-2528, 2012.

Ganesan et al., "Diffuse optical spectroscopic imaging of subcutaneous adipose tissue metabolic changes during weight loss," Int J Obes (Lond). Aug. 2016 ; 40(8). Author Manuscript available in PMC Oct. 22, 2016. pp. 1292-1300, Oct. 2016.

Gardner, et al., "Enhanced Umbilical Blood Flow During Acute HypoxemiaAfter Chronic Umbilical Cord Compression, A Role for Nitric Oxide," Basic Science Reports in Circulation, pp. 331-335, Jun. 30, 2003.

Gardosi, et al., "Adaptation of pulse oximetry for fetal monitoring during labour," The Lancet, 337: 1265-1267, May 25, 1991.

Gardosi, et al., "Continuous Intrapartum Monitoring Offectal Oxygen Saturation," The Lancet, Sep. 16, 1989, pp. 692-693.

Garite, et al., "Transactions of the Twentieth Annual Meeting of the Society for Maternal-Fetal Medicine—Continued," American Journal of Obstetrics and Gynecology, 183(5): 1049-1058, Nov. 2000.

Ghiasi, et al., "Transabdominal Fetal Oximetry, Project conducted at the Laboratory for Embedded and Programmable Systems," (LEPS), pp. 1-4.

Giordano, "New ANSI guidelines remind users to take stock of industrial laser protections," Laser Focus World, 50(10):41-43+47 • Oct. 2014.

Goodlin, "Preliminary experience with intrapartum fetal pulse oximetry in humans," Obstetrics and Gynecology, 82(2): 314-315, Jul. 31, 1993.

Graham, et al.,"A systematic review of the role of intrapartum hypoxia-ischemia in the causation of neonatal encephalopathy," American Journal of Obstetrics & Gynecology, pp. 587-595, Dec. 2008.

Greene, "Obstetricians Still Await a Deus ex Machina," The New England Journal of Medicine, 355: 2247-2248, Nov. 23, 2006.

Gregg, et al., "Brain specificity of diffuse optical imaging: improvements from superficial signal regression and tomography," Frontiers in NeuroEnergetics, 2(13), pp. 1-8, Jul. 14, 2010.

Grimes, et al., "Electronic Fetal Monitoring as a Public Health Screening Program: The Arithmetic of Failure," Obstetrics & Gynecology, 116(6): 1397-1400, Dec. 2010.

Gunn, et al., "Fetal Hypoxia Insults and Patterns of Brain Injury: Insights from Animal Models," Clin Perinatol, 36: 579-593, 2009.

Gutierrez—The Expanding Importance of Synthetic Data, 2022 https://opendatascience.com/the-expanding-importance-of-synthetic-data/ (Year: 2022).

Harini, et al., "Design and Implementation of a Calibration—Free Pulse Oximeter", In: Goh J. (eds) The 15th International Conference on Biomedical Engineering. IFMBE Proceedings, vol. 43, Springer, Cham, pp. 100-103, 2014.

Haydon, et al., "The effect of maternal oxygen administration on fetal pulse oximetry during labor in fetuses with honreassuring fetal heart rate patterns," American Journal of Obstetrics and Gynecology, 195: 735-738, 2006.

Haykin, In Kalman Filtering and Neural Networks, Ed. Simon Haykin, John Wiley & Sons, Inc., New York, NY, pp. 298, 2001.

Hiraoka, et al., "A Monte Carlo investigation of optical pathlength in inhomogeneous tissue and its application to hear-infrared spectroscopy," Institute of Physics and Engineering in Medicine, 38: 1859-1876, 1993.

Hyvärinen, "Fast and Robust Fixed-Point Algorithms for Independent Component Analysis," IEEE Trans. on Neural Networks, 10(3): 626-634, 1999.

International Commission on Non-Ionizing Radiation Protection (ICNIRP), "ICNIRP Guidelines on Limits of Exposure to Incoherent Visible and Infrared Radiation," Health Physics, 105(1): 74- 96; 2013.

International Search Report and the Written Opinion of the International Searching Authority for International Application No. PCT/US19/40639 dated Nov. 12, 2019.

International Search Report and the Written Opinion of the International Searching Authority for International Application No. PCT/US2017/062782, dated Feb. 19, 2018.

International Search Report and Written Opinion mailed Mar. 13, 2017, from the International Searching Authority, for International Patent Application No. PCT/US2016/068994 (filed Dec. 28, 2016), 13 pages.

Jacques, "Corrigendum: Optical properties of biological tissues: a review," IOP Publishing, Phys. Med. Biol. 58: 5007-5008, Jun. 27, 2013.

Jacques, "Optical properties of biological tissues: a review," IOP Publishing, Phys. Med. Biol. 58: R37-R61, May 10, 2013.

Jezewski, et al., "Extraction of Fetal Heart-Rate Signal as the Time Event Series From Evenly Sampled Data Acquired Using Doppler Ultrasound Technique," IEEE Transactions on Biomedical Engineering, 55(2): 805-810, Feb. 2008.

Johnson et al., "Continuous fetal monitoring with a pulse oximeter: a case of cord compression," Am. J. Obstet. Gynecol., 161(5): 1295-1296, Nov. 1989 (Abstract Only).

Johnson, et al., "Continuous Intrapartum Measurement of Fetal Oxygen Saturation," The Lancet, pp. 517, Aug. 27, 1988.

Johnson, et al., "Fetal monitoring with pulse oximetry," British Journal of Obstetrics and Gynaecology, 98: 36-41, Jan. 1991.

Julious, "Sample size of 12 per group rule ofthumb for a pilot study," Pharmaceut. Statist., 4: 287-291, 2005.

Jumadi, et al., Development of theoretical oxygen saturation calibration curve based on optical density ratio and optical simulation approach,: AIP Conference Proceedings 1883, pp. 1-11, Sep. 14, 2017.

Jumadi, et al., "Investigating the Effect of Total Radiated Power on Fetus Using Optical Simulation Approach Based on Exposure

(56) References Cited

OTHER PUBLICATIONS

Safety Limit for Eye and Tissue Injury," Journal of Life Sciences and Technologies, 2(1): 24-27, Jun. 2014.
Jumadi, et al., "Transabdominal Fetal Pulse Oximeter Using LEDs and Photodiode: A Design Consideration Study," 2015 2nd International Conference on Biomedical Engineering (ICoBE), pp. 1-6, Mar. 30-31, 2015.
Jurovata, et al., "Simulation of Photon Propagation in Tissue Using Matlab", Faculty of Materials Science and Technology in Trnava Slovak University of Techology in Bratislava, Research Papers (2013), 21:31-37.
Kainerstorfer, et al., "Optical oximetry of vol. oscillating vascular compartments: contributions from oscillatory blood flow," Journal of Biomedical Optics, 21(10): pp. 101408-1-101408-13, Oct. 2016.
Kelly, et al., "Dose-dependent relationship between acidosis at birth and likelihood of death or cerebral palsy," Arch Dis Child Fetal Neonatal Ed 2017, pp. F1-F6, 2017.
Kim, et al., "Noise reduction of PPG signal during Free Movements Using Adaptive SFLC (scaled Fourier linear combiner)," IFMBE proceedings, pp. 1083-1086, Jan. 2007.
Kirschbaum, et al., "Oxyhemoglobin dissociation characteristics of human and sheep maternal and fetal blood," Am. J. Obstetric and Gynecology, 96(5): 741-759, 1966.
Klauser, et al., "Use of fetal pulse oximetry among high-risk women in labor: A randomized clinical trial," American Journal of Obstetrics and Gynecology, 192: 1810-1817, 2005.
Kohl, et al., "Determination of the wavelength dependence of the differential pathlength factor from near-infrared pulse signals," Physics in Medicine & Biology, 43: 1771-1782, 1998.
Komalla, "A new method based on complex EMD for motion artifacts reduction in PPG signals for pulse oximeter application," Journal of Engineering Technology, Special Issue on Technology Applications and Innovations, 6: 187-200, 2017.
Konugolu Venkata Sekar, "Broadband Time-Domain Disffuse Optics for Clinical Diagnostics and Diffuse Raman Spectroscopy," Doctoral Dissertation, Politecnico de Milano, Physics Department, pp. 1-288, 2016.
Kuhnert, et al., "Intrapartum management of nonreassuring fetal heart rate patterns: A randomized controlled trial of fetal pulse oximetry," American Journal of Obstetrics and Gynecology, 191: 1989-1995, 2004.
Lakowicz, et al., "Frequency-Domain Measurements of Photon Migration in Tissues," Chemical Physics Letters, 166(3): 246-252, Feb. 23, 1990.
Laqua, et al., "A phantom with pulsating artificial vessels for non-invasive fetal pulse oximetry", Conf Proc IEEE Eng Med Biol Soc., pp. 5631-5634, 2014.
Laqua, et al., "FPGA controlled artificial vascular system," Current Directions in Biomedical Engineering, 1: 446-449, 2015.
Laqua, et al., "Improved FPGA controlled artificial vascular system for plethysmographic measurements", Current Directions in Biomedical Engineering, 2(1): 689-693, 2016.
Larosa, et al., "Understanding the full Spectrum of Organ Injury Following Intrapartum Asphyxia," Frontiers in Pediatrics, 5(16): 1-11, Feb. 17, 2017.
Larsen, "Pulse Oximetry Devices Market," Meddevicetracker, Pharma Intelligence, pp. 1-58, Dec. 2017.
Lear, et al., "The peripheral chemoreflex: indefatigable guardian offetal physiological adaptation to labour," The Journal of Physiology, pp. 1-13, 2018.
Lemieux, et al., "Investigating non-Gaussian scattering processes by using nth-order intensity correlation functions," 16(7): 1651-1664, Jul. 1999.
Leszczynska-Gorzelak, et al., "Intrapartum cardiotocography and fetal pulse oximetry in assessing fetal hypoxia," International Journal of Gynecology & Obstetrics, 76: 9-14, 2002.
Louie, et al., "Four Types of Pulse Oximeters Accurately Detect Hypoxia during Low Perfusion and Motion," Anesthesiology, pp. 1-11, 2017.

Luttkus, et al., "Pulse oximetry during labour—does it give rise to hope? Value of saturation monitoring in comparison to fetal blood gas status," European Journal of Obstetrics & Gynecology and Reproductive Biology, 110, pp. S132-S138, 2003.
Mallinckrodt, Inc., "(N-400) Fetal Oxygen Saturation Monitoring System," Summary of Safety and Effectivenes Information Data, pp. 31, 2000.
Mannheimer, et al., "Wavelength Selection for Low-Saturation Pulse Oximetry," IEEE Transactions on Biomedical Engineering, 44(3): 148-158, Mar. 1997.
Martinek, et al., "Non-Invasive Fetal Monitoring: A Maternal Surface ECG Electrode Placement-Based Novel Approach for Optimization of Adaptive Filter Control Parameters Using the LMS and RLS Algorithms," Sensors, 17: 1154, pp. 1-32, May 19, 2017.
Zourabian, et al., "Trans-abdominal monitoring of fetal arterial blood oxygenation using pulse oximetry," Journal of Biomedical Optics, 5(4): 391-405, Oct. 2000.
"Anesthesia for Fetal Procedures and Surgery," pp. 280-281.
"Assessing the Photobiological Safety of LEDs," pp. 1-8, 2012.
"Corometrics™ 250 Series Monitor Operator's Manual", GE Healthcare, Revision E (Apr. 28, 2009), 258 pgs.
"Fetal Pulse Oximetry System Clinical Use Guide", OxiFirst, Nellcor (2003), 60 pgs.
"Narrow beam LED in Dragon Dome package (850nm)", OSRAM Opto Semicondutors (Mar. 10, 2014), Version 1.3, SFH 4783, pp. 1-12.
"OSRAM Opto Semiconductors GF CSHPM1.24-3S4S-1", Mouser Electronics (accessed Dec. 2016), 2 pgs.
Aaronson, et al., "Android-Based Tocodynamometer and Fetal Heart Rate Monitor," Tocotronics (2013), 21 pgs.
Ahearne, et al., "Short and long term prognosis in perinatal asphyxia: An update," World Journal of Clinical Pediatrics, 5(1): 67-74, Feb. 8, 2016.
Aldrich, et al., "Late fetal heart decelerations and changes in cerebral oxygenation during the first stage of labour," British Journal of Obstetrics and Gynaecology, 102: 9-13, Jan. 1995.
Alfirevic, et al., "Continuous cardiotocography (CTG) as a form of electronicfetal monitoring (EFM) for fetal assessment during labour (Review)," Cochrane Database of Systematic Reviews 2017, Issue 2. Art. No. CD006066, pp. 1 to 56, 2017.
Amer, et al., "Xenon Combined With Hypothermia in Perinatal Hypoxic-Ischemic Encephalopathy: A Noble Gas, a Noble Mission," Pediatric Neurology, 84: 5-10, Jul. 2018.
Angelo, et al., "Review of structured light in diffuse optical imaging," Journal of Biomedical Optics 24(7), 071602 (Jul. 2019), 20 pages.
Arridge, "Inverse Problems in Optical Tomography," INI Cambridge, pp. 1-74, Aug. 24, 2011.
Arridge, "Optical tomography in medical imaging," Inverse Problems, 15: R41-R93, 1999.
Arridge, et al., "The theoretical basis for the determination of optical path lengths in tissue: temporal and frequency analysis," Physics in Medicine & Biology, 37(7): 1531-1560, 1992.
Ayres-De-Campos, "Electronic fetal monitoring orcardiotocography, 50 years later: what's in a name?," American Journal of Obstetrics & Gynecology, 218(6): 545-546, Jun. 2018.
Bansal, et al., "Wearable Organic Optoelectronic Sensors for Medicine," Advanced Materials (2014), 7 pgs.
Barry, et al., "The Pregnant Sheep as a Model for Human Pregnancy," Theriogenology, 69(1): 55-67, Jan. 1, 2008.
Bauer, et al., "Quantitative photoacoustic imaging:correcting for heterogeneous light fluence distributions using diffuse optical tomography," Journal of Biomedical Optics, 16(9): 096016-1-096016-7, Sep. 2011.
Belfort, et al., "A Randomized Trial of Intrapartum Fetal ECG ST-Segment Analysis," The New England Journal of Medicine, 373(7): 632-641, Aug. 13, 2015.
Bennet, et al., "The Cerebral Hemodynamic Response to Asphyxia and Hypoxia in the Near-term Fetal Sheep as Measured by Near Infrared Spectroscopy," Pediatric Research, 44: 951-957, Dec. 1, 1998.
Bennet, et al., "The Fetal Heart RateResponse to Hypoxia: Insights from Animal Models," Clin Perinatol, 36: 655-672, 2009.

(56) References Cited

OTHER PUBLICATIONS

Bevilacqua, et al., "In vivo local determination of tissue optical properties: applications to human brain, " Applied Optics, 38(22): 4939-4950, 1999.
Bloom, et al., "Fetal Pulse Oximetry and Cesarean Delivery," The New England Journal of Medicine, 355: 2195-2202, Nov. 23, 2006.
Bloom, et al., "Fetal Pulse Oximetry: Duration of Desaturation and Intrapartum Outcome," Journal of Obstetrics and Gynecology, 93(6): 1036-1040, Jun. 1999.
Bloom, et al., "What We Have Learned About Intrapartum Fetal Monitoring Trials in the MFMU Network," Author Manuscript, Semin Perinatol, 40(5): 307-317, Aug. 2016.
Boas, et al., "Diffuse optical imaging of brain activation: approaches to optimizing image sensitivity, resolution, and accuracy," NeuroImage, 23: S275-S288, 2004.
Boas, et al., "Scattering and Imaging with Diffusing Temporal Fields Correlation, " Physical Review Letters, 75(9): 1855-1859, Aug. 28, 1995.
Boas, et al., "Spatially varying dynamical properties of turbidmedia probed withdiffusing temporal light correlation," J. Opt. Soc. Am., 14(1): 192-215, Jan. 1997.
Bottrich, et al., "Signal Separation for Transabdominal Noninvasive Fetal Pulse Oximetry using Comb Filters," Conf Proc IEEE Eng Med Biol Soc, pp. 5870-5873, 2018.
Bozkurt, et al., "Safety assessment of near infrared light emitting diodes for diffuse optical measurements," BioMedical Engineering Online, 3(1): pp. 10, Mar. 22, 2004.
Buckley, et al., "Diffuse correlation spectroscopy formeasurement of cerebral blood flow: future prospects," Neurophotonics, 1(1), pp. 011009-1-011009-7, Jul.-Sep. 2014.
Buschmann, et al., "Fetal oxygen saturation measurement by transmission pulse oximetry," The Lancet, 339: 615, Mar. 7, 1992.
Cahill, et al., "A prospective cohort study of fetal heart rate monitoring: deceleration area is predictive of feal acidemia," American Journal of Obstetrics & Gynecology, 218(5), pp. 523.e1-523. e12, May 2018.
Caliskan, et al., "Reduction in caesarean delivery with fetal heartrate monitoring and intermittent pulse oximetryafter induction of labour with misoprostol," The Journal of Maternal-Fetal & Neonatal Medicine, 22(5): 445-451, May 2009.
Carbonne, et al., "Fetal pulse oximetry: correlation between changes in oxygen saturation and neonatal outcome. Preliminary report on 39 cases," European Journal of Obstetrics & Gynecology and Reproductive Biology, 57: 73-77, 1994.
Carbonne, et al., "Multicenter oximetry study on the clinical value of fetal pulse oximetry," Am J Obstet Gynecol, 177(3): 593-598, 1997.
Carter, et al., "Calibration of a Reflectance Pulse Oximeter in Fetal Lambs for Arterial Oxygen Saturations Below 70%," J Soc Gynecol Invest, 5(5): 255-259, Sep.-Oct. 1998.
Cerebral Palsy Guidance, Cerebral Palsy, Cerebral Palsy Guidance Website, pp. 1 to 14, 2018.
Chan, et al., "Effects of Compression on Soft Tissue Optical Properties," IEEE Journal of Selected Topics in Quantum Electronics, 2(4): 943-950, Dec. 1996.
Chandraharan, "Fetal scalp blood sampling during labour: is it auseful diagnostic test or a historical test that nolonger has a place in modern clinical obstetrics?" Royal College of Obstetricians and Gynaecologists, www.bjog.org, pp. 1056-1062, Mar. 6, 2014.
Cheung, et al., "In vivo cerebrovascular measurement combining diffuse near-infrared absorption and correlation spectroscopies," Physics in Medicine & Biology, 46: 2053-2065, 2001.
Choe, "Diffuse Optical Tomography and Spectroscopy of Breast Cancer and Fetal Brain," Pub'd, Sep. 29, 2005, A Dissertation in Physics and Astronomy, Faculties of the University of Pennsylvania.
Choe, et al., "Transabdominal near infrared oximetry of hypoxic stress in fetal sheep brain in utero," PNAS, 100(22): 12950-12954, Oct. 28, 2003.
Clark, et al., "Intrapartum management of category II fetal heart rate tracings: towards standardization of care," American Journal of Obstetrics & Gynecology, pp. 89-97, Aug. 2013.
Clark, et al., "The limits of electronic fetal heart rate monitoring in the prevention of neonatal metabolic acidemia," American Journal of Obstetrics & Gynecology, 216, pp. 163.e1-163.e6, Feb. 2017.
Colditz, et al., "Fetal pulse oximetry: Instrumentation and Recent Clinical Experience," Clinics in Perinatology, 26(4): 869-880, Dec. 1999.
Dassel, et al., "Reflectance Pulse Oximetry in Fetal Lambs," Pediatric Research, 31(3): 266-269, 1992.
De Blasi, et al., "Noninvasive measurement of human forearm oxygen consumption by near infrared spectroscopy," European Journal of Applied Physiology, 67: 20-25, 1993.
Delpy, et al., "Estimation of optical pathlength through tissue from direct time of flight measurement," Physics in Medicine & Biology, 33(12): 1433-1442, 1988.
Martinello, et al., "Management and investigation of neonatal-encephalopathy: 2017 update," Arch Dis Child Fetal Neonatal , 102: pp. F346-F-358, 2017.
Mawn, et al., "Trans-abdominal Monitoring of Fetal Arterial Oxygen Saturation Using Pulse Oximetry," IEEE EMBS-NEBE, 227-228, 2002.
McNamara, et al., "Continuous intrapartum pH, pO2, pCO2, and SpO2 monitoring," Obstet Gynecol Clin North Am, 26(4): 671-693, Dec. 1999.
Meschia, et al., "A Comparison of the Oxygen Dissociation Curves of the Bloods of Maternal, Fetal and Newborn Sheep At Various pHs," In: Oxgen Dissociation Curves in Sheep at Various pHs, pp. 95-97, Sep. 23, 1960.
Mesquita, et al., "Direct measurement of tissue blood flow and metabolism with diffuse optics," Philosophical Transactions of The Royal Society A, 369: 4390-4403, 2011.
Miller, "Raydiant Oximetry: Provides Crucial Comfort for New Mothers," MedTech Strategist, 5(4), pp. 2, Mar. 27, 2018.
Molavi, et al., "Motion Artifact Removal from Muscle NIR Spectroscopy Measurements," Conference paper in Canadian Conference on Electrical and Computer Engineering, pp. 1-5, May 2010.
Mourant, et al., "Mechanisms of light scattering from biological cells relevant to noninvasive optical-tissue diagnostics," Applied Optics, 37(15): 3586-3593, Jun. 1, 1998.
Nasiriavanaki, et al., "High-resolution photoacoustic tomography of resting-state functional connectivity in the mouse brain," PNAS, 111(1): 21-26, Jan. 7, 2014.
Nelson, et al., "Electronic fetal monitoring, cerebralpalsy, and caesarean section: assumptions versus evidence," BMJ, 355: pp. 1-3, Dec. 1, 2016.
Nioka, et al., "Fetal transabdominal pulse oximeter studies using a hypoxic sheep model," The Journal of Maternal-Fetal and Neonatal Medicine, 17(6): 393-399, Jun. 2005.
Nitzan, et al., "Calibration-Free Pulse Oximetry Based on Two Wavelengths in the Infrared—A Preliminary Study," Sensors 2014, 14: 7420-7434, Apr. 23, 2014.
Nonnenmacher, et al., "Predictive value of pulse oximetry for the development of fetal acidosis," J. Perinat. Med, 38: 83-86, 2010.
Noren, et al., "Reduced prevalence of metabolic acidosis at birth: an analysis of established STAN usage in the total population of deliveries in a Swedish district hospital," American Journal of Obstetrics & Gynecology, 202, pp. 546.e1-546.e7, Jun. 2010.
Novak, et al., "Perinatal Brain Injury Mechanisms, Prevention, and Outcomes," Clin Pernatol, 45: 357-375, 2018.
OBG Project, "Which Fetal Heart Monitoring Parameters Best Predict Fetal Acidemia?," https://www.obgproject.com/Category/Grandrounds/) pp. 1-2, date unknown.
Office Action mailed Feb. 1, 2018, from the Taiwan Intellectual Property Office, for Taiwan Patent Application No. 105143848, 17 pages.
Olutoye, et al., "Food and Drug Administration warning on anesthesia and brain development: implications for obstetric and fetal surgery," American Journal of Obstetrics & Gynecology, pp. 98-102, Jan. 2018.

(56) References Cited

OTHER PUBLICATIONS

Patient Safety Movement Foundation, "Actionable Patient Safety Solution (APSS) #11C: Reducing Unnecessary C-Sections," 2018 Patient Safety Movement Foundation, pp. 1-8, Aug. 15, 2018.
PCT International Search Report, International Searching Authority, for International Patent Application No. PCT/US2017/062782 filed on Nov. 21, 2017, pp. 1 to 4, Feb. 19, 2018.
PCT/US2018/068042 International Search Report and Written Opinion, Apr. 26, 2019, 16 pages.
PCT/US2018/068049 International Search Report and Written Opinion, Apr. 26, 2019, 20 pages.
Peat, et al., "Continuous intrapartum measurement of fetal oxygen saturation," The Lancet, Jul. 23, 1988, pp. 213.
Peebles, et al., "Effect of oxytocin on fetal brain oxgenation during labour," The Lancet, 338: 254-255, Jul. 27, 1991.
Peek, et al., "Fetal Pulse Oximetry and Cesarean Delivery," The New England Journal of Medicine, 356: 1377-1378, Mar. 29, 2007.
Pereira, et al., "Recognition of chronic hypoxia and pre-existing foetal injury on the cardiotocograph (CTG): Urgent need to think beyond the guidelines," Porto Biomedical Journal, 2(4): 124-129, 2017.
Peters, et al., "Beat-to-beat detection of fetal heart rate: Doppler ultrasound cardiotocography compared to direct ECG cardiotocography in time and frequency domain," Physiological Measurement, 25: 585-593, 2004.
Phelan, et al., "Fetal Heart Rate Observations in the Brain-Damaged Infant," Seminars in Perinatology, 24(3): 221-229, Jun. 2000.
Philips proprietary camera based monitoring technology is first in the world to measure absolute arterial blood oxygenation (SpO2) levels without ever touching the patient, Jun. 6, 2016, 4 pages (https://www.usa.philips.com/a-w/about/news/archive/standard/news/press/2016/20160606-philips-proprietary-camera-based-monitoring-technology-is-first-in-the-world-to-measure-absolute-arterial-blood-oxygenation-levels-without-ever-touching-the-patient.html) Jun. 6, 2016.
Pifferi, et al., "Real-time method for fitting time-resolved relectance and transmittance measurements with a Monte Carlo model," Applied Optics, 37(13): 2774-2776, May 1, 1998.
Porreco, et al., "Dystocia in nulliparous patients monitored with fetal pulse oximetry," American Journal of Obstetrics and Gynecology, 190: 113-117, 2004.
Ragozzino, et al., "Average Fetal Depth in Utero: Data for Estimation of Fetal Absorbed Radiation Dose," Radiology, 158(2): 513-515, 1986.
Ramanujam, et al., "Antepartum, Transabdominal Near Infrared Spectroscopy: Feasibility of Measuring Photon Migration Through the Fetal Head In Utero," The Journal of Maternal-Fetal Medicine, 8: 275-288, 1999.
Ramanujam, et al., "Photon migration through fetal head in utero using continuous wave, near infrared spectroscopy," Journal of Biomedical Optics, 5(2): 173-184, Apr. 2000.
Raydiant Oximetry, Inc.; International Application No. PCT/US2021/052092 filed Sep. 24, 2021, International Search Report and Written Opinion, ISAIUS, Dec. 23, 2021; 10 pp.
Rei, et al., "Neurological damage arising from intrapartum hypoxia/acidosis," Best Practice & Research Clinical Obstetrics and Gynaecology, 30: 79-86, 2016.
Ren, et al., "Quasi-simultaneous multimodal imaging of cutaneous tissue oxygenation and perfusion," Journal of Biomedical Optics, 20(12): pp. 121307-1 thru 121307-10, Dec. 2015.
Reuss, "Factors Influencing Fetal Pulse Oximetry Performance," Journal of Clinical Monitoring and Computing, 18: 13-24, 2004.
Reuss, "Multilayer Modeling of Reflectance Pulse Oximetry," IEEE Transactions on Biomedical Engineering, 52(2): 153-159, Feb. 2005.
Reuss, et al., "The pulse in reflectance pulse oximetry: modeling and experimental studies," Journal of Clinical Monitoring and Computing, 18: 289-299, 2004.

Rivolta, et al., "Acceleration and Deceleration Capacity of Fetal Heart Rate in an In-Vivo Sheep Model," PLOS One, 98(8): 1-10, Aug. 2014.
Roche-Labarbe, et al., "Noninvasive Optical Measures of CBV, StO2, CBF Index, and rCMRO2in Human Premature Neonates' Brains in the First Six Weeks of Life," Human Brain Mapping, 31: 341-352, 2010.
Roemer, et al., "Sensitivity, specificity, receiver-operating characteristic (ROC) curves and likelihood ratios for electronic foetal heart rate monitoring using new evaluation techniques," Z Geburtshilfe Neonatol, 214(3): 108-118, Jun. 2010 (Abstract Only).
Ross, "Labor and Fetal Heart Rate Decelerations: Relation to Fetal Metabolic Acidosis," Clinical Obstetrics and Gynecology, 54(1): 74-82, 2011.
Roth, et al., "Unequal Motherhood: Racial-Ethnic and Socioeconomic Disparities in Cesarean Sections in the United States," Social Problems, 59(2): 207-227, May 2012.
Saager, et al., "Direct characterization and removal of interfering absorption trends in two-layer turbid media," J. Opt. Soc. Am. A, 22(8): 1874-1882, Sep. 2005.
Sabiani, et al., "Intra- and interobserver agreement among obstetric experts in court regarding the review of abnormal fetal heart rate tracings and obstetrical management," American Journal of Obstetrics & Gynecology, 213(6): pp. 856.e1 thru 856.e8, Dec. 2015.
Saccone, et al., "Electrocardiogram ST Analysis During Labor A Systematic Review and Meta-analysis of Randomized Controlled Trials," Obstetrics & Gynecology, 127(1): 127-135, Jan. 2016.
Salamalekis, et al., "Computerised intrapartum diagnosis of fetal hypoxia based on fetal heart rate monitoring and fetal pulse oximetry recordings utilising wavelet analysis and neural networks," BJOG: an International Journal of Obstetrics and Gynaecology, 109: 1137-1142, Oct. 2002.
Salamalekis, et al., "Fetal pulse oximetry and wavelet analysis of the fetal heart rate in the evaluation of abnormal cardiotocography tracings," J. Obstet. Gynaecol. Res., 32(2): 135-139, Apr. 2006.
Sartwelle, et al., "A half century of electronic fetal monitoring and bioethics: silence speaks louder than words," Maternal Health, Neonatology, and Perinatology, 3:(21): 1-8, 2017.
Sartwelle, et al., "The Ethics of Teaching Physicians Electronic Fetal Monitoring: And Now for the Rest of the Story," Surg J, 3: pp. e42 thru e-47, 2017.
Sassaroli, et al., "Comment on the modified Beer-Lambert law for scattering media," Physics in Medicine & Biology, 49(14): pp. N255 thru N257, Jul. 5, 2004.
Scheeren et al.—Monitoring tissue oxygenation by near infrared spectroscopy (N IRS): background and current applications; J ClinManit Comput (2012) 26:279-287 (Year: 2012).
Schiermeier, et al., "Sensitivity and specificity of intrapartum computerised FIGO criteria for cardiotocography and fetal scalp pH during labour: multicentre, observational study," BJOG An International Journal of Obstetrics and Gynaecology, pp. 1557-1563, Aug. 26, 2008.
Schweiger, et al., "Near-infrared imaging: photon measurement density functions," Proc. SPIE, 2389: 366-377, May 30, 1995.
Seelbach-Göbel, et al., "The prediction of fetal acidosis by means of intrapartum fetalpulse oximetry," American Journal of Obstetrics and Gynecology, 180(1): 73-81, Jan. 1999.
Severinghaus, et al., "History of Blood Gas Analysis. VII. Pulse Oximetry," Journal of Clinical Monitoring, 3(2): 135-138, Apr. 1987.
Shang, et al., "Portable optical tissue flow oximeter based on diffuse correlation spectroscopy," Optics Letters, 34(22): 3556-3558, Nov. 15, 2009.
Siristatidis, et al., "Alterations in Doppler velocimetry indices of the umbilical artery during fetal hypoxia in labor, in relation to cardiotocography and fetal pulse oximetry findings," Arch Gynecol Obstet, 272: 191-195, 2005.
Siristatidis, et al., "Evaluation of fetal intrapartum hypoxia by middle cerebral and umbilical artery Doppler velocimetry with simultaneous cardiotocography and pulse oximetry," Arch Gynecol Obstet, 270: 265-270, 2004.

(56) References Cited

OTHER PUBLICATIONS

Siristatidis, et al., "Intrapartum Surveillance of IUGR Fetuses with Cardiotocography and Fetal Pulse Oximetry," Biology of the Neonate, 83: 162-165, 2003.
Spector-Bagdady, et al., "Clinician Self-Interestand the Case of Electronic Fetal Monitoring," Hastings Center Report, pp. 16-24, Nov.-Dec. 2017.
Spencer, et al., "MASS Spectrometer System for Continuous Skin-Surface and Intravascular Blood Gas Measurement of Maternal-Fetal Respiration in Labour," Journal of Biomedical Engineering, 9: 161-168, Apr. 1987.
Spong, et al., "Preventing the First Cesarean Delivery: Summary of a Joint Eunice Kennedy Shriver National Institute of Child Health and Human Development, Society for Maternal-Fetal Medicine, and American College of Obstetricians and Gynecologists Workshop," American Journal of Obstetrics and Gynecology, 120(5): 1181-1193, 2012.
Steinbrink, et al., "Illuminating the BOLD signal: combined fMRI-fNIRS studies," Magnetic Resonance Imaging, 24: 495-505, 2006.
Stipcevic et al., "Characterization of a novel avalanche photodiode for single photon detection in VIS-NIR range," Optics Express, 18(16): 17448-17459, Jul. 30, 2010.
Strangman, et al., "Factors affecting the accuracy of near-infrared spectroscopy concentration calculations for focal changes in oxygenation parameters," NeuroImage, 18: 865-879, 2003.
Subramaniam, "An IR Muscle Contraction Sensor", Cornell University, student project (last modified Jun. 10, 2014), retrieved from: https://people.ece.cornell.edu/land/courses/eceprojectsland/STUDENTPROJ/2013to2014/ras578/Writeup/An%20IR%20Muscle%20Contraction%20Sensor.html, 6 pgs., Feb. 2017.
Sutin, et al., "Time-domain diffuse correlation spectroscopy," Optica, vol. 3, Issue 9, pp. 1006-1013, Sep. 2016.
Tamborini, et al., "Development and characterization of a multi distance and multi wave length diffuse correlation spectroscopy system," Neurophoton, 5(1), pp. 011015-1 thru 011015-10, Jan.-Mar. 2018.
Themelis, et al., "Near-infrared spectroscopy measurement of the pulsatile component of cerebral blood flow and volume from arterial oscillations," Journal of Biomedical Optics, 21(1), pp. 1-15, 2007.
Tomich, "Fetal heart rate monitoring," Power Point—Department of Obstetrics and Gynecology, University of Nebraska College of Medicine, (uploaded Jul. 30, 2014) 69 pages.
Torbenson, et al., "Intrapartum factors associated with neonatal hypoxic ischemic encephalopathy: a case-controlled study," BMC Pregnancy and Childbirth, 17(415): 1-7, 2017.
Townsend, et al., "Pulse Oximetry," Medical Electronics, Michaelmas Term, 2001.
Truven Health Analytics, The cost of having a baby in the United States,: Truven Health Analytics Marketscan® Study, pp. 1 to 84, 2014.
Truven Health Analytics, The Cost of Having a Baby in the United States—Executive Summary, Truven Health Analytics Marketscan Study, pp. 5, Jan. 2013.
Tu, et al., "An Analytical Model for Optimization of Frequency-domain System," Bioengineering Conference, 2002. Proceedings of the IEEE 28th Annual Northeast, pp. 79-80, 2002.
Uchida, et al., "Reevaluation of intrapartum fetal monitoring using fetaloximetry: A review," The Journal of Obstetrics and Gynaecology Research, pp. 1-8, 2018.
Ultman, et al., "Differential Pathlength Factor for Diffuse Photon Scattering Through Tissue by a Pulse-Response Method," 107: 73-82, 1991.
Valverde, et al., "Effectiveness of pulse oximetry versus fetal electrocardiograma intrapartum evaluation of non reassuring fetal heart rate," European Journal of Obstetric and Gynecology and Reproductive Biology, 159: 333-337, 2011.
Van 'T Hooft, In "Improving evaluation of obstetric interventions," University of Amsterdam Dissertation, pp. 1-243, 2016.
Verkruysse, et al., "Calibration of Contactless Pulse Oximetry," Anesthesia & Analgesia, 124(1): 136-145, Jan. 2017.
Vidaeff, et al., "Fetal pulse oximetry: 8 vital questions," OBG Management, pp. 28-44, Mar. 2004.
Vintzileos, et al., "Transabdominal fetal pulse oximetry with near-infrared spectroscopy," American Journal of Obstetrics and Gynecology, 192: 129-133, 2005.
Vishnoi et al., "Photon migration through fetal head in utero using continuous wave, near-infrared spectroscopy: development and evaluation of experimental and numerical models", J. Biomedical Optics 5(2): 163-172, Apr. 2000.
Weyrich, et al., "Development of a Phantom to Modulate the Maternal and Fetal Pulse Curve for Pulse Oximetry Measurements," Biomed Tech 57 (Suppl. 1): 803-806, 2012.
Willmann, et al., "Small-volume frequency-domain oximetry: phantom experiments and first in vivo results," Journal of Biomedical Optics, 8(4): 618-628, Oct. 2003.
Wolfberg, "The Future of Fetal Monitoring," Reviews in Obstetrics & Gynecology, 5(3/4), pp. e132 thru e136, 2012.
Woo, et al., "Achieving higher-value obstetrical care," American Journal of Obstetrics & Gynecology, pp. 250-255 and 250.e1 thru 250.e8, Mar. 2017.
XP the Xperts in Power, 400-2500 Watts fleX, 400-2500 Watts fleXPower Series, Product information sheet, xppower.com, pp. 1 to 10, Jan. 5, 2016.
Yamaleyeva, et al., "Photoacoustic imaging for in vivo quantification of placental oxygenation in mice," The FASEB Journal, 31(12): 5520-5529, 2017.
Yamashiro, E., et al., "Fetal tolerance of maternal resuscitative endovascular balloon occlusion of the aorta in a sheep model," Am. J. Obstetrics & Genecology, Supplemental to Jan. 2020, pp. S718-S719, Jan. 2020.
Yan, et al., "Reduction of motion artifact in pulse oximetry by smoothed pseudo Wigner-Ville distribution," Journal of NeuroEngineering and Rehabilitation, 2(3), pp. 1-9, Mar. 1, 2005.
Yousefi, et al., "Adaptive Cancellation of Motion Artifact in Wearable Biosensors," 34th Annual International Conference of the IEEE Embs, San Diego, California USA, Aug. 28-Sep. 1, 2012, pp. 5.
Yuan, et al., "Motion Artefact Minimisation from Photoplethysmography based Non-invasive Hemoglobin Sensor by the Envelope Method," Measurements, 115, pp. 1-18, Feb. 2018 (Draft Only).
Zhang, et al., "Adaptive filtering for global interference cancellation and real-time recovery of evoked brain activity: a Monte Carlo simulation study," Journal of Biomedical Optics, 12(4), pp. 044014-1 thru 044014-12, Jul./Aug. 2007.
Zhao, et al., "In vivo determination of the optical properties of infant brain using frequency-domain near-infrared spectroscopy," Journal of Biomedical Optics, 10(2), pp. 024028-1 thru 024028-7, Mar./Apr. 2005.
Zhao, et al., "Quantitative real-time pulse oximetry with ultrafast frequency frequency-domain diffuse optics and deep neural network processing," Biomedical Optics Express, 9(12): 5997-6008, 2018.
Zijistra, et al., "Absorption Spectra of Human Fetal and Adult Oxyhemoglobin, De-Oxyhemoglobin, Carboxyhemoglobin, and Methemoglobin," Clinical Chemistry, 37(9): 1633-1638, 1991.

500

Receive sets of simulated light transmission data and/or sets of simulated detected electronic signals, corresponding oximetry values, and optional additional information
505

Divide the simulated light transmission data sets and/or sets of detected electronic signals and corresponding oximetry values into a training set of simulated data and a testing set of simulated data
510

Determine, set, and/or select machine learning inputs for a machine learning architecture for generation of a simulated fetal oximetry model
515

Train a simulated fetal oximetry model by running training data set through the machine learning architecture
520

Training complete?
525 — No → (back to 520)
Yes ↓

Test the simulated fetal oximetry model using the testing data set
530

Evaluate the results of testing of the simulated fetal oximetry model
535

Testing complete?
540 — No → (back to 530)
Yes ↓

Tune the simulated fetal oximetry model responsively to the evaluation
545

705 Receive sets of simulated light transmission data and/or sets of detected electronic signals, corresponding oximetry values, and optional additional information

710 Determine, set, and/or select machine learning inputs for a machine learning architecture for generation of a simulated fetal oximetry model

715 Train a simulated fetal oximetry model by running simulated light transmission data sets and corresponding oximetry values through the machine learning architecture

720 Training complete? No → (back to 715); Yes ↓

725 Store the simulated fetal oximetry model

730 Receive instructions for adapting the tuned simulated fetal oximetry model to generate an in vivo fetal oximetry model

735 Adapt tuned simulated fetal oximetry model for transfer to an in vivo fetal oximetry model

740 Receive a plurality of sets of measured in vivo light transmission data and corresponding measured oximetry values

745 Training an in vivo fetal oximetry model by running in vivo training data set through the machine learning architecture

750 Training complete? No → (back to 745); Yes ↓

755 Finalize the in vivo fetal oximetry model 805 or end

| Values | Wavelengths | Source-Detector Distance | Fetal Cardiac State | Maternal Cardiac State | Fetal Depth | Fetal SpO2 | Maternal SpO2 | Fetal Scattering Coefficient Multiplier | Maternal Scattering Coefficient Multiplier | Number of Combinations |
|---|---|---|---|---|---|---|---|---|---|---|
|  | 740 | 30 | 0 | 0 | 20 | 0.2 | 0.9 | 0.5 | 1 |  |
|  | 755 | 40 | 0.01 | 0.01 | 25 | 0.3 | 0.98 | 1 | 1.25 |  |
|  | 810 | 45 | 0.02 | 0.02 | 32 | 0.4 |  | 1.5 | 1.6 |  |
|  | 840 | 50 |  |  | 40 | 0.5 |  | 2 | 2 |  |
|  |  | 55 |  |  | 48 | 0.6 |  |  | 2.3 |  |
|  |  | 65 |  |  |  |  |  |  |  |  |
|  |  | 75 |  |  |  |  |  |  |  |  |
| Number of Parameters | 4 | 7 | 3 | 3 | 5 | 5 | 2 | 4 | 5 | 84,000 |

SYSTEMS, DEVICES, AND METHODS FOR DEVELOPING A MODEL FOR USE WHEN PERFORMING OXIMETRY AND/OR PULSE OXIMETRY AND SYSTEMS, DEVICES, AND METHODS FOR USING A FETAL OXIMETRY MODEL TO DETERMINE A FETAL OXIMETRY VALUE

RELATED APPLICATION

This application is a continuation of application Ser. No. 17/804,555, filed May 27, 2022, which is a continuation of application number PCT/US2021/052092, filed Sep. 24, 2021, which is an international patent application of, and claims priority to, U.S. Provisional Patent Application No. 63/083,064 filed 24 Sep. 2020 and entitled "SYSTEMS, DEVICES, AND METHODS for DEVELOPING A MODEL FOR USE WHEN PERFORMING OXIMETRY AND/OR PULSE OXIMETRY," which is incorporated herein in its entirety.

FIELD OF INVENTION

The present invention is in the field of medical devices, oximetry, pulse oximetry, and machine learning, more particularly, in the fields using machine learning to develop a model to determine and/or predict fetal oximetry values using measured light transmission data, wherein a portion of the measured light transmission data includes light transmission data for light incident on a fetus within a pregnant mammal's abdomen. The present invention is also directed to using a fetal oximetry model to determine and/or predict fetal oximetry values using measured light transmission data.

BACKGROUND

Oximetry is a method for determining the oxygen saturation of hemoglobin in a mammal's blood. Typically, 90% (or higher) of an adult human's hemoglobin is saturated with (i.e., bound to) oxygen while only 30-60% of a fetus's blood is saturated with oxygen. Pulse oximetry is a type of oximetry that uses changes in blood volume through a heartbeat cycle to internally calibrate hemoglobin oxygen saturation measurements of the arterial blood.

Current methods of monitoring fetal health, such as monitoring fetal heart rate, are inefficient at determining levels of fetal distress and, at times, provide false positive results indicating fetal distress that may result in the unnecessary performance of a Cesarean delivery.

SUMMARY

Described herein are systems, devices, and methods for using simulated light transmission data and associated simulated fetal oximetry values (e.g., fetal hemoglobin oxygen saturation levels and/or fetal tissue oxygen saturation levels) to train a simulated fetal oximetry model. The training may be accomplished using, for example, machine learning, artificial intelligence, a neural network, an artificial neural network, a Bayesian network, and/or deep learning (a portion, or all, of which may be collectively referred to herein as "machine learning"). In some cases, a simulated and/or in vivo fetal oximetry model (as will be discussed below) may be include a plurality of layers and/or functions including, but not limited to, input layers, output layers, confounding factor layers, calculation layers, noise reduction layers, filtering layers, layers regarding an isolation of a fetal portion of light transmission data (e.g., light transmission data that may represent a pulsatile signal of only the fetus) from composite light transmission data that may represent a pulsatile signal of both the pregnant mammal and the fetus, calibration layers, maternal characteristic layers, and/or fetal characteristic layers. In some instances, a simulated and/or in vivo fetal oximetry model may be developed using convolution.

The simulated light transmission data may be generated via the running simulations of plurality of optical inputs through a model of animal tissue (also referred to herein as a "tissue model"). In some embodiments, the simulated light transmission data may be a simulated electronic signal similar to a detected electronic signal generated by a photodetector upon detection of an optical signal (e.g., photons) that may have been incident upon the tissue being modeled (e.g., a pregnant mammal's abdomen and fetus) and then conversion of the detected optical signal into a digital signal. Stated differently, simulated light transmission data may correspond to a simulated electronic signal that is similar to an electronic signal that may be provided by a photodetector upon detection of an optical signal that has traveled through tissue (like the modeled tissue) and conversion of the detected optical signal into a corresponding electronic signal. Often times, the tissue model has at least two layers of tissue and/or blood that may be circulating through tissue that may have different optical properties and, in some instances, one of the layers models/corresponds to maternal tissue (e.g., maternal blood, skin, abdominal wall, uterus, and/or a combination of one or more tissue layers) and another of the layers models/corresponds to fetal tissue (e.g., fetal blood, skin, bone, or neural tissue, and/or a combination thereof). The simulated fetal oximetry model may then be used as a basis to train an in vivo fetal oximetry model using measured in vivo light transmission data and fetal oximetry values via, for example, a process of transfer learning.

This two-step process is beneficial because generating and/or obtaining measured in vivo data sufficient to train a fetal oximetry model from scratch is very difficult given, for example, the number of data points that must be measured and the complexity/cost of obtaining the measured data points. In order to train a fetal oximetry model using only measured in vivo data, a sufficient number (e.g., 5,000-10,000,000) of measured oximetry values in a healthy state (e.g., fetal oxygenation levels are sufficient) and a disease state (e.g., fetal hypoxia and/or fetal hypoxemia) and corresponding light transmission data must be measured and input into the machine learning/model training architecture to train a fetal oximetry model that outputs sufficiently accurate predictions of fetal oximetry values using light transmission data measured in a clinical setting. Currently, measuring fetal oximetry values requires either analysis of a fetal scalp sample taken in-utero, a blood gas analysis conducted on umbilical cord blood following birth or in-utero, and/or a fetal oximetry measurement obtained via an oximeter placed directly on the fetal skin (e.g., cheek or head) via inserting the oximeter into the pregnant mammal's endocervical canal so that it may directly contact the fetal skin. The difficulty of obtaining fetal oximetry measurements along with the relative rarity of fetuses in a disease state provides substantial, even insurmountable, obstacles to obtaining sufficient measured in vivo data to train a fetal oximetry model to predict a fetal oximetry value when given measured light transmission data.

The presently disclosed method solves this problem by using simulated light transmission data and corresponding simulated fetal oximetry values to supply the data needed to train a simulated fetal oximetry model without the need to collect in vivo measure data. This greatly shortens the timeline needed to generate the simulated fetal oximetry model because simulated light transmission data and corresponding simulated fetal oximetry values may be virtually generated relatively quickly using tissue models and simulations without the need to perform invasive and costly medical procedures on a fetus. In addition, the use of simulated light transmission data and corresponding simulated fetal oximetry values allows for the modeling of a variety of scenarios that may occur so rarely clinically that it may take many years to capture sufficient data from these scenarios with which to train a fetal oximetry model solely using measured in vivo data.

By using simulated light transmission data and corresponding simulated fetal oximetry values to train a simulated fetal oximetry model, adapting the simulated fetal oximetry model so that it may be trained using measured in vivo data, and then training an in vivo fetal oximetry model using measured in vivo data, the a timeline for process of generating a valid and clinically useful fetal oximetry model is greatly shorted and is more accurate because a portion (e.g., 40-95%) of the training of the in vivo fetal oximetry model is already completed via the training of the simulated fetal oximetry model without the need for costly and difficult to obtain measured in vivo data.

The methods disclosed herein may be executed by processors, or networks of processors, that are configured to perform machine learning and/or deep machine learning processes to develop predictive models, in this case models that can receive light transmission data that includes light that was incident on a fetus, analyze the light transmission data, and predict a fetal oximetry value with sufficient precision to be clinically useful when, for example, determining whether a fetus is in distress during, for example, gestation and/or a labor and delivery process. In some cases the processors, or networks of processors may reside in a cloud computing environment. In some embodiments, the processor is and/or includes a machine learning architecture.

In some embodiments, a plurality of sets of simulated light transmission data and corresponding oximetry values for each set of simulated light transmission data may be received. At times, a fetal oximetry value for each set of simulated light transmission data may be calculated using the respective set of simulated light transmission data via, for example, the Beer-Lambert Law or modified Beer-Lambert Law. Each set of the simulated light transmission data may have been generated by simulating a transmission of light through a model of animal tissue, wherein the model includes at least two layers of animal tissue with one of the layers of the model of animal tissue modeling fetal tissue. In some embodiments, each layer of the animal tissue model may have different optical properties (e.g., absorption, scattering, etc.).

In some instances, the plurality of sets of simulated light transmission data may include simulated light transmission data for light of one or more wavelengths or distinct ranges of wavelengths such as light with a wavelength within a range of 620 nm-670 nm, 920 nm-970 nm, 640 nm-660 nm, or 940-960 nm. Additionally, or alternatively, the simulated light may be of a broadband (e.g., white light) of wavelengths.

A simulated fetal oximetry model may then be trained using the plurality of sets of simulated light transmission data and corresponding oximetry values by, for example, inputting the plurality of sets of simulated light transmission data and corresponding oximetry values into a machine learning architecture. The simulated fetal oximetry model may include a plurality of layers and/or functions and may be configured to receive light transmission data and determine an oximetry value for a fetus using the received light transmission data.

Instructions to adapt the simulated fetal oximetry model for transfer to an in vivo fetal oximetry model may be received and, once the simulated fetal oximetry model is sufficiently trained using the sets of simulated light transmission data, the simulated fetal oximetry model may be adapted for transfer to an in vivo fetal oximetry model responsively to the instructions.

In some embodiments, an instruction to adapt the simulated fetal oximetry model for transfer to an in vivo fetal oximetry model may be received. These instructions may include instructions to fix, or lock, one or more layers of the simulated fetal oximetry model (e.g. an input layer, a calibration layer, a maternal characteristic layer, a fetal characteristic layer, a noise cancelling layer, etc.) that are generally applicable to the in vivo fetal oximetry model so that the fixed layers do not change during the training process for the in vivo fetal oximetry model. Exemplary inputs to the one or more fixed layers of the simulated fetal oximetry model may correspond to a calibration factor for determining an oximetry value, a wavelength, or a range of wavelengths, of light in the simulated light transmission data from a given distance between a source and a detector, a fetal depth and/or a physiological and/or geometrical characteristic of the pregnant mammal and/or fetus A plurality of sets of measured in vivo light transmission data corresponding light traveling through and being emitted from (e.g., via backscattering) an abdomen of a pregnant mammal and her fetus may then be received. Each set of measured in vivo light transmission data may correspond to a fetal oximetry value, which may also be received. Then, an in vivo fetal oximetry model may be generated and/or trained by inputting the plurality of sets of measured in vivo light transmission data and corresponding measured fetal oximetry values into the adapted simulated fetal oximetry model. Once training of the in vivo fetal oximetry model is complete, it may be stored in a database and/or an indication that the training of the in vivo fetal oximetry model is complete may be provided to a user via, for example, a display device.

In some instances, the plurality of sets of measured, in vivo light transmission data may include light transmission data for light of one or more wavelengths or distinct ranges of wavelengths such as light with a wavelength within a range of 620 nm-670 nm, 920 nm-970 nm, 640 nm-660 nm, or 940-960 nm. Additionally, or alternatively, the simulated light may be of a broadband (e.g., white light) of wavelengths.

In some embodiments, the fetal oximetry values may be fetal hemoglobin oxygen saturation values and a set of measured light transmission data for a pregnant mammal may be received. The light may have been incident on the pregnant mammal's abdomen and a fetus positioned within the pregnant mammal's abdomen. A fetal hemoglobin oxygen saturation value may be determined for the fetus' blood by inputting the set of measured light transmission data into the in vivo fetal oximetry model. The fetal hemoglobin oxygen saturation value for the fetus' blood may then be communicated to a display device.

Additionally, or alternatively, the fetal oximetry values may be fetal tissue oxygen saturation values and a set of measured light transmission data for a pregnant mammal incident on the pregnant mammal's abdomen and a fetus positioned within the pregnant mammal's abdomen. A fetal tissue oxygen saturation value for a portion of fetal tissue may them be determined by inputting the set of measured light transmission data into the in vivo fetal oximetry model. The fetal tissue oxygen saturation value for the portion of fetal tissue may then be communicated to a display device.

Additionally, or alternatively, an additional plurality of sets of measured in vivo light transmission data for light traveling through an abdomen of the pregnant mammal may be received. At least some of the measured in vivo light transmission data may correspond to light incident on the fetus and, at times, a portion of the light transmission data corresponding to light that is isolated from light incident only on the pregnant mammal so that a pulsatile signal of the fetus and/or tissue of the fetus may be isolated from the light transmission data. The in vivo fetal oximetry model may then be updated by inputting the additional plurality of sets of measured in vivo light transmission data and corresponding measured fetal oximetry values into the in vivo fetal oximetry model, thereby generating an updated in vivo fetal oximetry model. The updated in vivo fetal oximetry model may be stored in a database and/or used to predict a fetal oximetry value using in vivo light transmission data measured in, for example, a clinical setting.

In some cases, the training of the simulated fetal oximetry model may include using machine learning to train the simulated fetal oximetry model. Additionally, or alternatively, the training of the in vivo fetal oximetry model may include using machine learning to train the in vivo fetal oximetry model.

At times, the in vivo fetal oximetry model may be configured to receive measured in vivo light transmission data and predict fetal hypoxia and/or fetal hypoxemia using the received measured in vivo light transmission data.

Additionally, or alternatively, the wherein in vivo fetal oximetry model may be configured to receive measured in vivo light transmission data and predict a fetal oximetry value using the received measured in vivo light transmission data.

In some embodiments, a fetal oximetry value predicted by the in vivo fetal oximetry model may be compared to a threshold fetal oximetry value and an indication of the comparison to a display device. At times, the indication is an alert when, for example, the fetal oximetry value is below the threshold fetal oximetry value. In some instances, the set of measured light transmission data may be a first set of measured light transmission data and the determined fetal oximetry value may be a first determined oximetry value and a second set of measured light transmission data for a pregnant mammal may be received. A second fetal oximetry value may then be determined for the fetus by inputting the second set of measured light transmission data into the in vivo fetal oximetry model. A relationship (e.g., a trend) between the first and second fetal oximetry values may be determined and then an indication of the relationship to a display device.

In some embodiments, systems, devices, and methods may be configured so that light transmission data corresponding to an optical signal that is detected by a photodetector and converted into the light transmission data is received by a processor. The optical signal may be a composite of light that is incident on a pregnant mammal's abdomen and a fetus contained within the pregnant mammal's abdomen. The light transmission data may be input into an in vivo fetal oximetry model that has been trained using simulated light transmission data. An output from the in vivo fetal oximetry model, the output including an indication of an oximetry value for the fetus. The oximetry value may be, for example, a level of fetal hemoglobin oxygen saturation, and/or a level of fetal tissue oxygen saturation.

At times, the systems, devices, and/or methods disclosed herein may be configured to isolate a portion of the light transmission data that corresponds to light that was incident on the fetus and thereby generate a fetal signal prior to inputting the light transmission data into the in vivo fetal oximetry model, wherein the fetal signal is input into the in vivo fetal oximetry model.

Additionally, or alternatively, in some embodiments, the in vivo fetal oximetry model may be iteratively tuned, over time and clinical usage with additional measured in vivo light transmission data.

In some embodiments, the systems, devices, and/or methods disclosed herein may be configured to provide an indication of the oximetry value for the fetus to a display device and/or store an indication of the oximetry value for the fetus in a database.

In some embodiments, the systems, devices, and/or methods disclosed herein may be configured to determine whether the fetus has fetal hypoxia and/or fetal hypoxemia using the fetal oximetry value and an indication of this determination may be provided to a display device.

Additionally, or alternatively, the systems, devices, and/or methods disclosed herein may be configured to compare a predicted fetal oximetry value to a threshold fetal oximetry value and provide an indication of the comparison to a display device. In some instances, the indication is an alert when the fetal oximetry value is below the threshold fetal oximetry value.

Exemplary devices disclosed herein include 1) a communication interface configured to communicate with a display device and a source of light transmission data to receive a set of light transmission data; 2) a memory having an in vivo fetal oximetry model stored thereon; and 3) a processor configured to receive light transmission data from the communication interface, access the in vivo fetal oximetry model stored in the memory, predict a fetal oximetry value by inputting the received light transmission data into the in vivo fetal oximetry model, and communicate an indication of the fetal oximetry value to the display device.

In some embodiments, the processor may be further configured to isolate a portion of the light transmission data that corresponds to light that was incident on the fetus, thereby generating a fetal signal prior to inputting the light transmission data into the in vivo fetal oximetry model, wherein the fetal signal is input into the in vivo fetal oximetry model. Additionally, or alternatively, the processor may be further configured to store an indication of the fetal oximetry value for the fetus in a database.

Exemplary systems disclosed herein may include a fetal hemoglobin probe, a memory having an in vivo fetal oximetry model stored thereon, and a processor configured to receive light transmission data from the communication interface, access the in vivo fetal oximetry model stored in the memory, predict a fetal oximetry value by inputting the received light transmission data into the in vivo fetal oximetry model, and communicate an indication of the fetal oximetry value to the display device in accordance with one or more embodiments disclosed herein. The fetal hemoglobin probe may include, for example, one or more light source(s) configured to shine light into a pregnant mammal's abdomen and a fetus contained therein, one or more detectors (e.g., photodetectors) configured to detect light, from the light source, emanating from the pregnant mammal's abdomen and fetus and convert the detected light into light transmission data, and a communication interface configured to communicate the light transmission data to a processor.

BRIEF DESCRIPTION OF THE FIGURES

The present invention is illustrated by way of example, and not limitation, in the figures of the accompanying drawings in which:

FIG. 5 is a flowchart illustrating a process for the generation of a tuned simulated fetal oximetry model, consistent with some embodiments of the present invention;

FIG. 7 is a flowchart illustrating an exemplary process for the generation of an in vivo fetal oximetry model, consistent with some embodiments of the present invention;

FIG. 10 is a table of an exemplary set of parameters, in accordance with some embodiments of the present invention.

Figure 1A:
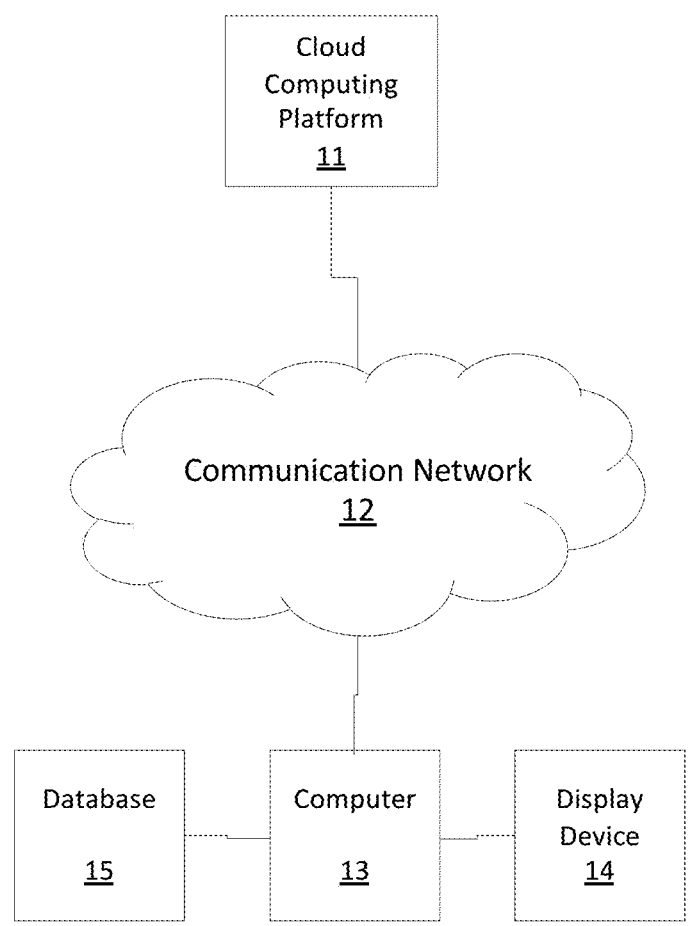
FIG. 1A is a block diagram illustrating an exemplary system for developing a model to accurately calculate fetal oxygen saturation in-utero, consistent with some embodiments of the present invention.

Throughout the drawings, the same reference numerals and characters, unless otherwise stated, are used to denote like features, elements, components, or portions of the illustrated embodiments. Moreover, while the subject invention will now be described in detail with reference to the drawings, the description is done in connection with the illustrative embodiments. It is intended that changes and modifications can be made to the described embodiments without departing from the true scope and spirit of the subject invention as defined by the appended claims.

WRITTEN DESCRIPTION

Near-IR spectroscopy, and pulse oximetry calculations, to estimate a percentage of oxygen bound to hemoglobin in the blood (also referred to herein as "hemoglobin oxygen saturation" or "SpO2") may incorporate calculations using the modified Beer Lambert law (mBLL), which describes changes in hemoglobin absorption related to changes in light intensity of various wavelengths. Under the assumption that bulk tissue has homogenous characteristics, the modified Beer Lambert law can be written as Equation 1:

$$\Delta\mu_a(\lambda) = -\frac{1}{r*DPF(\lambda)} \frac{I_{d(\lambda)} - I_{s(\lambda)}}{I_{s(\lambda)}} = -\frac{1}{r*DPF(\lambda)}\Delta OD \qquad \text{Equation 1}$$

Where:
$I_d$=diastolic intensity of the fetal pulse
$I_s$=systolic intensity of the fetal pulse
r=source detector distance, which may be given by the geometry of an optical probe or source/detector combination
DPF=differential path length factor, which is not known
$\Delta OD$=change in optical density
$\Delta\mu_a$=change in absorption coefficient
$\lambda$=wavelength Results from this equation may be used to extract values for concentrations of oxygenated hemoglobin (sometimes referred to herein as "c_HbO") and deoxygenated hemoglobin (sometimes referred to herein as "c__Hb") 2 according to Equation 2, below.

$$SpO2(\%)=c\_HbO/(c\_HbO+c\_Hb) \qquad \text{Equation 2}$$

Although the modified Beer Lambert Law traditionally serves as the fundamental basis for near-IR spectroscopy, it is limited by several assumptions, including that light absorption within tissue is homogeneous, change in a differential path length factor is negligible, and that the light scattering within tissue is low. In complex in vivo, physio-optical environments of, for example, non-homogenous tissue and/or two or more layers of different types of tissue such as a fetus within a mother, these assumptions may not always hold true and yield accurate calculations. For example, traditional methods for calculating pulse oximetry using the modified Beer Lambert Law assume that photons travel a relatively short distance (e.g., 1 cm) and that there is a negligible change in the differential path length factor (DPF) across this distance. However, when a distance photons travel is larger than 1 cm (e.g., 1.5-10 cm) changes in the DPF can be significant thereby adversely impacting the accuracy SpO2 calculations. For example, in transabdominal fetal application, photons can travel 5 cm, 10 cm, or more and, consequently, changes in the DPF can be significant. To accurately account for DPF variability and calculate oxygen saturation is a complex problem, particularly when multiple wavelengths of light are used. One way to overcome this problem is to calculate SpO2 using a 2-layer description of the modified Beer Lambert Law that can independently calibrate for different layers of tissue.

However, a drawback of the using the two-layer Modified Beer Lambert Law calculations when calculating oxygen saturation of target tissue is that this approach is dependent on having an accurate depth of the target (e.g., a fetus) within the body input in order to accurately calculate the blood oxygen saturation. This may pose a challenge in a clinical situation because measuring (via, for example, an ultrasound or Doppler device) depth of a target (e.g., a fetus, fetal head, or fetal back) within a body is open to clinical interpretation and may not always be reliable, especially when differences of as little as 5 mm can impact the accuracy of calculations. Furthermore, a target's depth that is measured by an ultrasound or Doppler device may not accurately reflect that path of the photons because, for example, the photons are a different signal type (i.e., optical) than the sound waves used by the ultrasound/Doppler device and/or the ultrasound/Doppler device is not positioned where the optical probe is positioned so the ultrasound/Doppler device may be imaging a portion of the surface tissue that is not coincident with the placement of the optical probe. In order to overcome the target depth requirement, machine learning may be deployed as a methodology to develop a model that augments the 2-layered description of the modified Beer Lambert Law to arrive at target SpO2 values without requiring target depth as an input. This model would them be able to accurately determine fetal oximetry values without requiring fetal depth.

Transdermal in vivo measurements of target (e.g., fetal) SpO2 levels may involve placing an optical probe (e.g., one or more light source(s) and photodetector(s)) on the skin of a patient (e.g., a pregnant woman), transmitting an optical signal into the skin of the patient, and collecting resulting optical signals emitted from the skin of the patient via, for example, backscattering and/or transmission through the patient's non-target tissue and target's tissue. In many cases, determining SpO2 involves calculating the amplitudes of the AC signals, normalizing them using (dividing by) the amplitude of the DC signals, and multiplying the normalized AC signals by a calibration factor that takes into account, for example, abdominal and/or fetal tissue scattering properties and/or fetal depth as a function of wavelength of the incident optical signal/light. However, this normalization methodology is, in many cases, too generic of an approach because, for example, the impact of the maternal/fetal tissue on the behavior of the incident light is uniform along the pathlength of the optical signal. However, in many cases, this is inaccurate due to one or more confounding influences of, for example, maternal tissue, maternal physiology, maternal movement, and/or fetal tissue/physiology/movement when the optical probe is being used and/or during measurement of fetal SpO2. Hence, a different normalization methodology for the AC signals may assist with more accurately calculating fetal SpO2.

In some embodiments, using one or more optical probe(s) that include multiple light sources (also called "sources" herein) and/or multiple photodetectors (also called "detectors" herein) that facilitate multiple sets of sources and detectors that have different source-detector distances (i.e., different distances between the source and detector) may provide inputs that can be used to compensate for confounding influences in some situations because, for example, a mean depth of penetration for the light into the patient's tissue (e.g., pregnant mammal's abdomen) gets larger as the source-detector separation increases. Shorter separations between the source and detector result in light that penetrates the tissue less deeply than light from larger separations between the source and detector. Use of signals detected when the source/detector distance is relatively short biases these measurement towards measuring only the patient's non-target (e.g., maternal or abdominal) tissues (which are shallower than the target tissue), because the light detected by relatively close detectors only penetrates the patient's non-target tissue. In some cases, these detected signals may be called short separation signals.

Additionally, or alternatively, by using one or more probes with various source/detector distances both the patient's non-target-only signals (i.e., short separation signals) and a composite signal that includes light incident on both the patient's non-target and target tissue (sometimes referred to herein as a "composite signal") may enable measurement and/or comparisons of variability of the patient's non-target and/or target tissue. In some instances, comparing detected signals from detectors with a short source/detector distance with detected signals from detectors with a longer source/detector distance may facilitate understanding of how the patient's non-target and/or target tissue my impact the behavior of light incident thereon. This information may be used, for example, to normalize AC signals and/or develop or adjust a calibration factor used to determine target SpO2, which may make calculation of target SpO2 more accurate than previously used techniques.

In, for example, a transabdominal fetal oximetry context, using machine learning as a methodology to develop a model that augments the 2-layered (one maternal and one fetal) description of the modified Beer Lambert Law to arrive at fetal hemoglobin oxygen saturation values without requiring fetal depth as an input and/or incorporates confounding influences of maternal and fetal tissue when determining fetal SpO2 requires a large data set of fetal SpO2 values so that many different scenarios with different fetal depths and/or confounding factors may be understood and factored into a determination of fetal SpO2 in a particular situation. A data set of fetal oximetry and/or SpO2 values calculated using a model, or mathematical simulation, of the fetal and/or maternal tissue, which is sometimes referred to herein as "calculated fetal oximetry values" or "calculated fetal Spo2 values," may be used to train and/or test a processor to determine fetal SpO2 values. In some instances, the model may be a physiological model of the fetus and mother, which in some cases may include static and time variant tissue layer properties of the fetus and/or pregnant mammal that may calculate how light may behave when transmitted and/or detected with various source-separation distances and light wavelengths. These calculated SpO2 values may, in some cases, represent a simulated light transmission time series data set ("also referred to herein as a "simulated light transmission data set") that models the optical signals that may be detected by a detector over time and may thereby be available for analysis, manipulation, and input into machine learning models in a manner similar to, for example, actual light transmission data sets collected from a detector and/or actual fetal SpO2 values. In some embodiments, simulated light transmission data used to calculate fetal oximetry and/or SpO2 values may be determined and/or generated using machine learning equipment and/or techniques.

Additionally, or alternatively, the simulated light transmission data may be generated by software designed to build models and/or generate simulated data for light traveling through tissue and/or tissue model(s). Examples of this software are Monte Carlo simulations and Near Infrared Fluorescence and Spectral Tomography (NIRFAST, Dartmouth College, NH) software. Use of modeling software allows for models to be built that incorporate a variety of parameters such as wavelength of light used, DFP, source/detector distance, and/or maternal and/or fetal morphological, geometric and/or physiological parameters such as abdominal wall thickness and/or composition, tissue composition, tissue type, muscular state of the maternal uterus, maternal skin color, fetal skin color, and/or position on the fetus on which the light was incident. At times, the parameters of the data sets and/or inputs used to generate the models may be changed discretely, randomly, pseudo-randomly, and/or selected within a range and/or distribution of values. Additionally, or alternatively, combinations of input parameters may be used to generate the simulated signals. This approach and/or a combination of approaches may provide a random covering of the possible simulated light transmission data sets/time series and/or calculated fetal SpO2 values that may be used for training and testing the machine learning model. Additionally, or alternatively, features may be extracted from simulated light transmission data sets to be used as inputs to the machine learning architecture or models. Examples of potential features that may be extracted from simulated light transmission data sets are correlation amplitudes, FFTs, DC levels, AC levels or other post-processed signal descriptors.

Possible uses and/or advantages of the present invention include, but are not limited to, facilitation of perturbation analysis of the data sets whereby one variable (e.g., maternal heart rate, fetal heart rate, fetal distance, source/detector distance) is changed at a time to determine an impact (if at all) on the calculated fetal SpO2 values. This is a substantial advantage over experimentally determined data sets, or calculated fetal SpO2 values, because it is difficult, in real life, to control only one factor at a time because, often times, multiple factors change at unpredictable rates/times with in vivo situations.

Additionally, or alternatively, the present invention may be used to perform sensitivity analysis, which may allow for changing multiple variables/parameters used to generate the models and/or simulated light transmission data sets so that, for example, the results (e.g., calculated fetal SpO2 values) may be evaluated for accuracy and/or to determine how multiple variables may interact with one another to vary calculated fetal SpO2 values. Model variables that may be modified to perform sensitivity analysis include, but are not limited to, noise, wavelength of light used, DFP, source/detector distance, and/or maternal and/or fetal morphological, geometric and/or physiological parameters such as abdominal wall thickness and/or composition, tissue composition, tissue type, muscular state of the maternal uterus, maternal skin color, fetal skin color, and/or position on the fetus on which the light was incident.

Additionally, or alternatively, an advantage of the present invention is that use of simulated light transmission data sets and/or fetal SpO2 values calculated using the simulated light transmission data sets to train a simulate fetal oximetry model, or teach the machine, reduces the number of experimentally, or measured, in vivo light transmission data sets and/or fetal SpO2 values that are necessary to arrive at an accurately trained model. This, in turn, reduces the need for a very large and difficult to obtain data set of actual fetal SpO2 values determined using measured/in vivo data (e.g., a blood gas analysis).

FIG. 1A provides an exemplary system 10 for using machine learning to develop a simulated fetal oximetry model and/or an in vivo fetal oximetry model as disclosed herein. In some cases, the developed simulated fetal oximetry model and/or an in vivo fetal oximetry model may compensate for one or more physio-optical influences that occur when performing transabdominal fetal oximetry. System 10 includes a cloud computing platform 11, a communication network 12, a computer 13, a display device 14, and a database 15. In many instances, communication network 12 is the Internet. The components of system 10 may be coupled together via wired and/or wireless communication links. In some instances, wireless communication of one or more components of system 10 may be enabled using short-range wireless communication protocols designed to communicate over relatively short distances (e.g., BLUETOOTH®, near field communication (NFC), radio-frequency identification (RFID), and Wi-Fi) with, for example, a computer or personal electronic device (e.g., tablet computer or smart phone) as described below.

Cloud computing platform 11 may be any cloud computing platform 11 configured to run a machine learning program and/or support a machine learning architecture such as TensorFlow. Exemplary cloud computing platforms include, but are not limited to, Amazon Web Service (AWS), Rackspace, and Microsoft Azure. Exemplary machine learning architectures include neural networks, artificial neural networks, Bayesian networks, and/or software or hardware that utilizes artificial intelligence.

Computer 13 may be configured to act as a communication terminal to cloud computing platform 11 via, for example, communication network 12 and may facilitate provision of the results machine learning calculations (e.g., training and/or testing of a simulated fetal oximetry model, tuning of a simulated fetal oximetry model, training and/or testing of a in vivo fetal oximetry model, and/or tuning of the in vivo fetal oximetry model) performed on cloud computing platform 11 to display device 155. Exemplary computers 13 include desktop and laptop computers, servers, tablet computers, personal electronic devices, mobile devices (e.g., smart phones), and the like. Exemplary display devices 155 are computer monitors, tablet computer devices, and displays provided by one or more of the components of system 10. In some instances, display device 155 may be resident in computer 13. Computer 13 may be communicatively coupled to database 15, which may be configured to store information (e.g., simulated optical inputs, simulated light transmission data sets, levels of a simulated fetal oximetry model, simulated and/or calculated fetal oximetry values, in vivo light transmission data sets, levels of an in vivo fetal oximetry model, model testing results, etc.), or inputs, used for machine learning and/or sets of instructions for computer 13 and/or cloud computing platform 11.

Figure 1B:
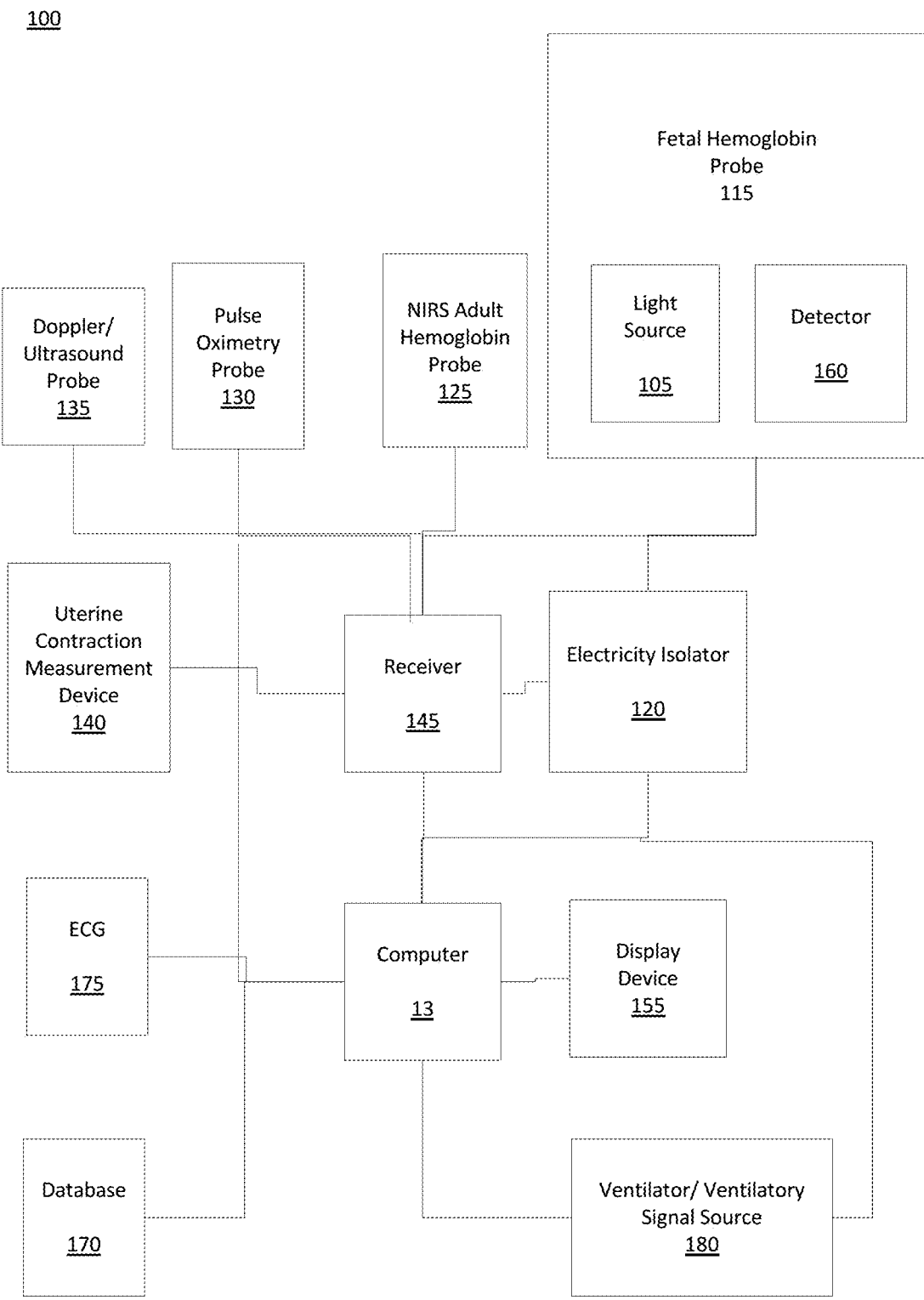
FIG. 1B is a block diagram of an exemplary system 100 for detecting and/or determining fetal hemoglobin oxygen saturation levels, consistent with some embodiments of the present invention.

FIG. 1B is a block diagram of an exemplary system 100 for measuring in vivo light transmission data, measuring in vivo fetal oximetry values, and/or determining in vivo fetal oximetry values. In some embodiments, system 100 and/or a component thereof, such as computer 13, may be communicatively coupled to system 10, or a component thereof such as communication network 12 and/or cloud computing platform 11. The components of system 100 may be coupled together via wired and/or wireless communication links. In some instances, wireless communication of one or more components of system 100 may be enabled by using short-range wireless communication protocols designed to communicate over relatively short distances (e.g., BLUETOOTH®, near field communication (NFC), radio-frequency identification (RFID), and Wi-Fi) with, for example, a computer or personal electronic device (e.g., tablet computer or smart phone) as described below.

System 100 includes a light source 105 and a detector 160 that, at times, may be housed in a single housing, which may be referred to as a fetal probe 115. Light source 105 may include a single, or multiple light sources and detector 160 may include a single, or multiple detectors.

Light sources 105 may transmit light at light of one or more wavelengths, including NIR, into the pregnant mammal's abdomen. Typically, the light emitted by light sources 105 will be focused or emitted as a narrow beam to reduce spreading of the light upon entry into the pregnant mammal's abdomen. Light sources 105 may be, for example, a LED, and/or a LASER, a tunable light bulb and/or a tunable LED that may be coupled to a fiber optic cable. On some occasions, the light sources may be one or more fiber optic cables optically coupled to a laser and arranged in an array. In some instances, the light sources 105 may be tunable or otherwise user configurable while, in other instances, one or more of the light sources may be configured to emit light within a pre-defined range of wavelengths. Additionally, or alternatively, one or more filters (not shown) and/or polarizers may filter/polarize the light emitted by light sources 105 to be of one or more preferred wavelengths. These filters/polarizers may also be tunable or user configurable.

An exemplary light source 105 may have a relatively small form factor and may operate with high efficiency, which may serve to, for example, conserve space and/or limit heat emitted by the light source 105. In one embodiment, light source 105 is configured to emit light in the range of 770-850 nm. Exemplary flux ratios for light sources include, but are not limited to a luminous flux/radiant flux of 175-260 mW, a total radiant flux of 300-550 mW and a power rating of 0.6 W-3.5 W.

Detector 160 may be configured to detect a light signal emitted from the pregnant mammal and/or the fetus via, for example, transmission and/or back scattering. Detector 160 may convert this light signal into an electronic signal, which may be communicated to a computer or processor and/or an on-board transceiver that may be capable of communicating the signal to the computer/processor. This emitted light might then be processed in order to determine how much light, at various wavelengths, passes through the fetus and/or is reflected and/or absorbed by the fetal oxyhemoglobin and/or de-oxyhemoglobin so that a fetal hemoglobin oxygen saturation level may be determined. This processing will be discussed in greater detail below. In some embodiments, detector 160 may be configured to detect/count single photons. At times, the optical signals detected by detector 160 and converted into an electronic signal corresponding to the detected optical signal may be referred to herein as measured, or in vivo, light transmission data and/or a detected electronic signal.

Exemplary detectors include, but are not limited to, cameras, traditional photomultiplier tubes (PMTs), silicon PMTs, avalanche photodiodes, and silicon photodiodes. In some embodiments, the detectors will have a relatively low cost (e.g., $50 or below), a low voltage requirement (e.g., less than 100 volts), and non-glass (e.g., plastic) form factor. In other embodiments, (e.g., contactless pulse oximetry) a sensitive camera may be deployed to receive light emitted by the pregnant mammal's abdomen. For example, detector 160 may be a sensitive camera adapted to capture small changes in fetal skin tone caused by changes in cardiovascular pressure associated with fetal myocardial contractions. In these embodiments, detector 160 and/or fetal probe 115 may be in contact with the pregnant mammal's abdomen, or not, as this embodiment may be used to perform so-called contactless pulse oximetry. In these embodiments, light sources 105 may be adapted to provide light (e.g., in the visible spectrum, near-infrared, etc.) directed toward the pregnant mammal's abdomen so that the detector 160 is able to receive/detect light emitted by the pregnant mammal's abdomen and fetus. The emitted light captured by detector 160 may be communicated to computer 13 for processing to convert the images to a measurement of fetal hemoglobin oxygen saturation according to, for example, one or more of the processes described herein.

A fetal probe 115, light source 105, and/or detector 160 may be of any appropriate size and, in some circumstances, may be sized so as to accommodate the size of the pregnant mammal using any appropriate sizing system (e.g., waist size and/or small, medium, large, etc.). Exemplary lengths for a fetal probe 115 include a length of 4 cm-40 cm and a width of 2 cm-10 cm. In some circumstances, the size and/or configuration of a fetal probe 115, or components thereof, may be responsive to skin pigmentation of the pregnant mammal and/or fetus. In some instances, the fetal probe 115 may be applied to the pregnant mammal's skin via tape or a strap that cooperates with a mechanism (e.g., snap, loop, etc.) (not shown). In some instances, fetal probe 115 may act to pre-process or filter detected signals.

System 100 includes a number of optional independent sensors/probes designed to monitor various aspects of maternal and/or fetal health and may be in contact with a pregnant mammal. These probes/sensors are a NIRS adult hemoglobin probe 125, a pulse oximetry probe 130, a Doppler and/or ultrasound probe 135, and a uterine contraction measurement device 140. Not all embodiments of system 100 will include all of these components. In some embodiments, system 100 may also include an electrocardiography (ECG) machine (not shown) that may be used to determine the pregnant mammal's and/or fetus's heart rate and/or an intrauterine pulse oximetry probe (not shown) that may be used to determine the fetus's heart rate. The Doppler and/or ultrasound probe 135 may be configured to be placed on the abdomen of the pregnant mammal and may be of a size and shape that approximates a silver U.S. dollar coin and may provide information regarding fetal position, orientation, and/or heart rate. Pulse oximetry probe 130 may be a conventional pulse oximetry probe placed on pregnant mammal's hand and/or finger to measure the pregnant mammal's hemoglobin oxygen saturation. NIRS adult hemoglobin probe 125 may be placed on, for example, the pregnant mammal's 2nd finger and may be configured to, for example, use near infrared spectroscopy to calculate the ratio of adult oxyhemoglobin to adult de-oxyhemoglobin. NIRS adult hemoglobin probe 125 may also be used to determine the pregnant mammal's heart rate.

Optionally, system 100 may include a uterine contraction measurement device 140 configured to measure the strength and/or timing of the pregnant mammal's uterine contractions. In some embodiments, uterine contractions will be measured by uterine contraction measurement device 140 as a function of pressure (e.g., measured in e.g., mmHg) over time. In some instances, the uterine contraction measurement device 140 is and/or includes a tocotransducer, which is an instrument that includes a pressure-sensing area that detects changes in the abdominal contour to measure uterine activity and, in this way, monitors frequency and duration of contractions.

In another embodiment, uterine contraction measurement device 140 may be configured to pass an electrical current through the pregnant mammal and measure changes in the electrical current as the uterus contracts. Additionally, or alternatively, uterine contractions may also be measured via near infrared spectroscopy using, for example, light received/detected by detector 160 because uterine contractions, which are muscle contractions, are oscillations of the uterine muscle between a contracted state and a relaxed state. Oxygen consumption of the uterine muscle during both of these stages is different and these differences may be detectable using NIRS.

Measurements and/or signals from NIRS adult hemoglobin probe 125, pulse oximetry probe 130, Doppler and/or ultrasound probe 135, and/or uterine contraction measurement device 140 may be communicated to receiver 145 for communication to computer 13 and display on display device 155 and, in some instances, may be considered secondary signals. As will be discussed below, measurements provided by NIRS adult hemoglobin probe 125, pulse oximetry probe 130, a Doppler and/or ultrasound probe 135, uterine contraction measurement device 140 may be used in conjunction with fetal probe 115 to isolate a fetal pulse signal and/or fetal heart rate from a maternal pulse signal and/or maternal heart rate. Receiver 145 may be configured to receive signals and/or data from one or more components of system 100 including, but not limited to, fetal probe 115, NIRS adult hemoglobin probe 125, pulse oximetry probe 130, Doppler and/or ultrasound probe 135, and/or uterine contraction measurement device 140. Communication of receiver 145 with other components of system may be made using wired or wireless communication.

In some instances, one or more of NIRS adult hemoglobin probe 125, pulse oximetry probe 130, a Doppler and/or ultrasound probe 135, uterine contraction measurement device 140 may include a dedicated display that provides the measurements to, for example, a user or medical treatment provider. It is important to note that not all of these probes may be used in every instance. For example, when the pregnant mammal is using fetal probe 115 in a setting outside of a hospital or treatment facility (e.g., at home or work) then, some of the probes (e.g., NIRS adult hemoglobin probe 125, pulse oximetry probe 130, a Doppler and/or ultrasound probe 135, uterine contraction measurement device 140) of system 100 may not be used.

In some instances, receiver 145 may be configured to process or pre-process received signals so as to, for example, make the signals compatible with computer 13 (e.g., convert an optical signal to an electrical signal), improve signal to noise ratio (SNR), amplify a received signal, etc. In some instances, receiver 145 may be resident within and/or a component of computer 13. In some embodiments, computer 13 may amplify or otherwise condition the received detected signal so as to, for example, improve the signal-to-noise ratio.

Receiver 145 may communicate received, pre-processed, and/or processed signals to computer 13. Computer 13 may act to process the received signals, as discussed in greater detail below, and facilitate provision of the results to a display device 155. Exemplary computers 13 include desktop and laptop computers, servers, tablet computers, personal electronic devices, mobile devices (e.g., smart phones), and the like. Exemplary display devices 155 are computer monitors, tablet computer devices, and displays provided by one or more of the components of system 100. In some instances, display device 155 may be resident in receiver 145 and/or computer 13. Computer 13 may be communicatively coupled to database 170, which may be configured to store information regarding physiological characteristic and/or combinations of physiological characteristic of pregnant mammals and/or their fetuses, impacts of physiological characteristic on light behavior, information regarding the calculation of hemoglobin oxygen saturation levels, calibration factors, and so on.

In some embodiments, a pregnant mammal may be electrically insulated from one or more components of system 100 by, for example, an electricity isolator 120. Exemplary electricity insulators 120 include circuit breakers, ground fault switches, and fuses.

In some embodiments, system 100 may include an electro-cardiogram (ECG) machine 175 configured to ascertain characteristics of the pregnant mammal's heart rate and/or pulse and/or measure same. These characteristics may be used as, for example, a secondary signal and/or maternal heart rate signal as disclosed herein.

In some embodiments, system 100 may include a ventilatory/respiratory signal source 180 that may be configured to monitor the pregnant mammal's respiratory rate and provide a respiratory signal indicating the pregnant mammal's respiratory rate to, for example, computer 13. Additionally, or alternatively, ventilatory/respiratory signal source 180 may be a source of a ventilatory signal obtained via, for example, cooperation with a ventilation machine. Exemplary ventilatory/respiratory signal sources 180 include, but are not limited to, a carbon dioxide measurement device, a stethoscope and/or electronic acoustic stethoscope, a device that measures chest excursion for the pregnant mammal, and a pulse oximeter. A signal from a pulse oximeter may be analyzed to determine variations in the PPG signal that may correspond to respiration for the pregnant mammal. Additionally, or alternatively, ventilatory/respiratory signal source 180 may provide a respiratory signal that corresponds to a frequency with which gas (e.g., air, anesthetic, etc.) is provided to the pregnant mammal during, for example, a surgical procedure. This respiratory signal may be used to, for example, determine a frequency of respiration for the pregnant mammal.

In some embodiments, system 100 may include a timestamping device 185. Timestamping device 185 may be configured to timestamp a signal provided by, for example, fetal probe 115, Doppler/ultrasound probe 135, pulse oximetry probe 130, NIRS adult hemoglobin probe, uterine contraction measurement device 140, ECG 175, and/or ventilatory/respiratory signal source 180 with a timestamp that represents, for example, an event (e.g., time, or t, =0, 10, 20, etc.) and/or chronological time (e.g., date and time). Timestamping device 185 may time stamp a signal via, for example, introducing a ground signal into system 100 that may simultaneously, or nearly simultaneously, interrupt or otherwise introduce a stamp or other indicator into a signal generated by one or more of, for example, fetal probe 115, Doppler/ultrasound probe 135, pulse oximetry probe 130, NIRS adult hemoglobin probe, uterine contraction measurement device 140, ECG 175, and/or ventilatory/respiratory signal source 180. Additionally, or alternatively, timestamping device 185 may time stamp a signal via, for example, introducing an optical signal into system 100 that may simultaneously, or nearly simultaneously, interrupt or otherwise introduce a stamp or other indicator into a signal generated by one or more of, for example, fetal probe 115, pulse oximetry probe 130, NIRS adult hemoglobin probe, uterine contraction measurement device 140. Additionally, or alternatively, timestamping device 185 may time stamp a signal via, for example, introducing an acoustic signal into system 100 that may simultaneously, or nearly simultaneously, interrupt or otherwise introduce a stamp or other indicator into a signal generated by one or more of, for example, fetal probe 115, Doppler/ultrasound probe 135, and/or ventilatory/respiratory signal source 180.

A timestamp generated by timestamping device 185 may serve as a simultaneous, or nearly simultaneous starting point, or benchmark, for the processing, measuring, synchronizing, correlating, and/or analyzing of a signal from, for example, fetal probe 115, Doppler/ultrasound probe 135, pulse oximetry probe 130, NIRS adult hemoglobin probe, uterine contraction measurement device 140, ECG 175, and/or ventilatory/respiratory signal source 180. In some instances, a time stamp may be used to correlate and/or synchronize two or more signals generated by, for example, fetal probe 115, Doppler/ultrasound probe 135, pulse oximetry probe 130, NIRS adult hemoglobin probe, uterine contraction measurement device 140, ECG 175, and/or ventilatory/respiratory signal source 180 so that, for example, they align in the time domain.

Figure 2:
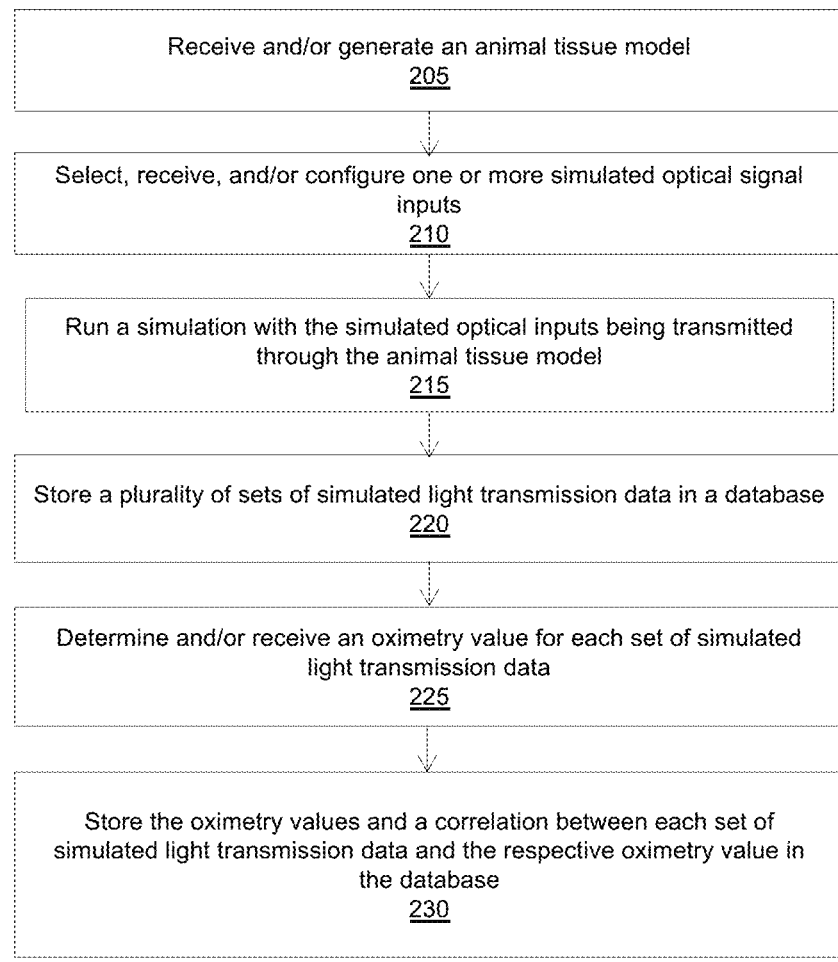
FIG. 2 is a flowchart showing an exemplary process for generating a plurality of sets of simulated light transmission data and corresponding oximetry values using a computer-generated model of animal tissue, consistent with some embodiments of the present invention.

FIG. 2 is a flowchart showing an exemplary process 200 for generating a plurality of sets of simulated light transmission data and corresponding oximetry values using a computer-generated, or simulated, model of animal tissue. Process 200 may be executed by, for example, system 100, 10, and/or components thereof.

Initially, in step 205, a two and/or three-dimensional model of a portion of animal tissue may be generated and/or received. The layers of the model may each have different optical properties such as absorption and/or reflection characteristics, blood saturation characteristics, in some cases, these optical properties may be dictated by properties of the tissue such as lipid content, water content, density, and/or tissue type. When process 200 is executed multiple times, one or more aspects of the model received and/or generated in step 205 may change.

Figure 9:
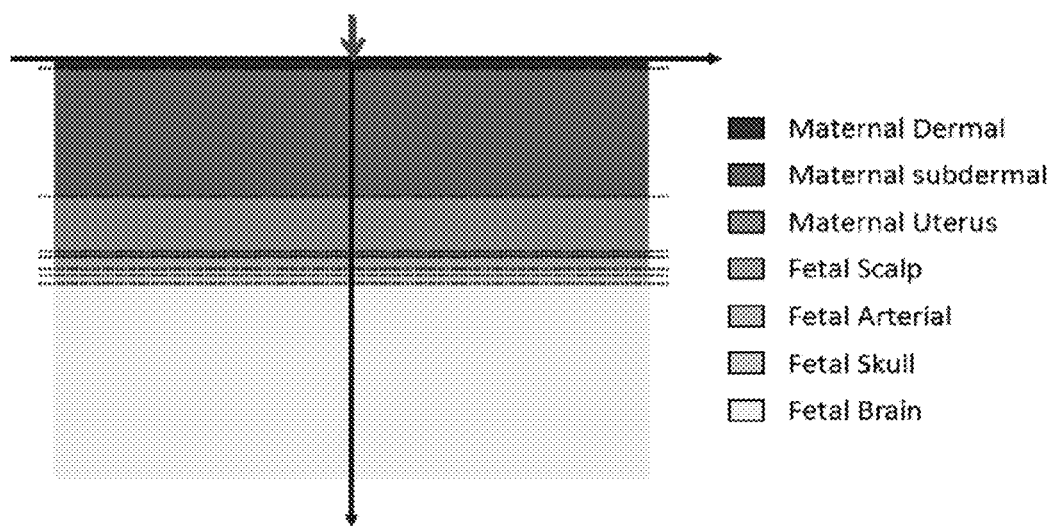
FIG. 9 is a diagram showing an exemplary seven-layer two-dimensional model of a pregnant mammal's abdomen and fetus is shown, in accordance with some embodiments of the present invention.

The model(s) of step 205 may include, for example, 1-8 layers of tissue; some of which may be fetal tissue. In many embodiments, the modeled tissue may include at least two layers one of which corresponds to maternal tissue and the other layer corresponds to fetal tissue. FIG. 9 provides an image of an exemplary seven-layer two-dimensional model 900 of a pregnant mammal's abdomen and her fetus that may be received and/or generated at step 205. The seven layers of two-dimensional model 900 are 1) maternal dermal, 2) maternal subdermal, 3) maternal uterus, 4) fetal scalp, 5) fetal arterial, 6) fetal skull, and 7) fetal brain. Each of these layers may have different optical properties based on, for example, light wavelength, light intensity, tissue layer composition, tissue layer thickness, and/or tissue layer geometry.

In some cases, execution of step 205 may also include receipt and/or selection of parameters or rules for the model, some of which may be machine learning inputs and/or optical properties of one or more layers of the model. FIG. 10 provides a table of exemplary parameters 1000 that may be used to generate a model in step 205 and/or may govern one or more aspects and/or functions of a model that is received. When a generated model is received in step 205 (as opposed to generated), a table like the table of FIG. 10 may also be received so that one or more parameters of the model may be understood. In some embodiments, one or more parameters of a model may dictate behavior of one or more simulated light transmission data sets.

The matrix of properties of table 1000 may be used to generate a two- and/or three-dimensional model, like exemplary model 900, of the pregnant mammal and/or fetus, which may then be used to generate a plurality of simulated light transmission data sets. More specifically, table 1000 provides exemplary values for wavelength of light emitted by the source, a distance between the source and a detector, fetal cardiac state, maternal cardiac state, fetal depth, fetal SpO2, maternal SpO2, fetal scattering coefficient multiplier, and maternal scattering coefficient multiplier. Additionally, or alternatively, other parameters may be used to generate the models such as tissue composition (e.g., lipid content, water content, muscle cell content, etc.), noise, ambient light, geometry of the portion of the human body being modeled, fetal and maternal cross correlation with heartbeats, DC level, normalization ratios, and/or fetal depth.

Figure 11:
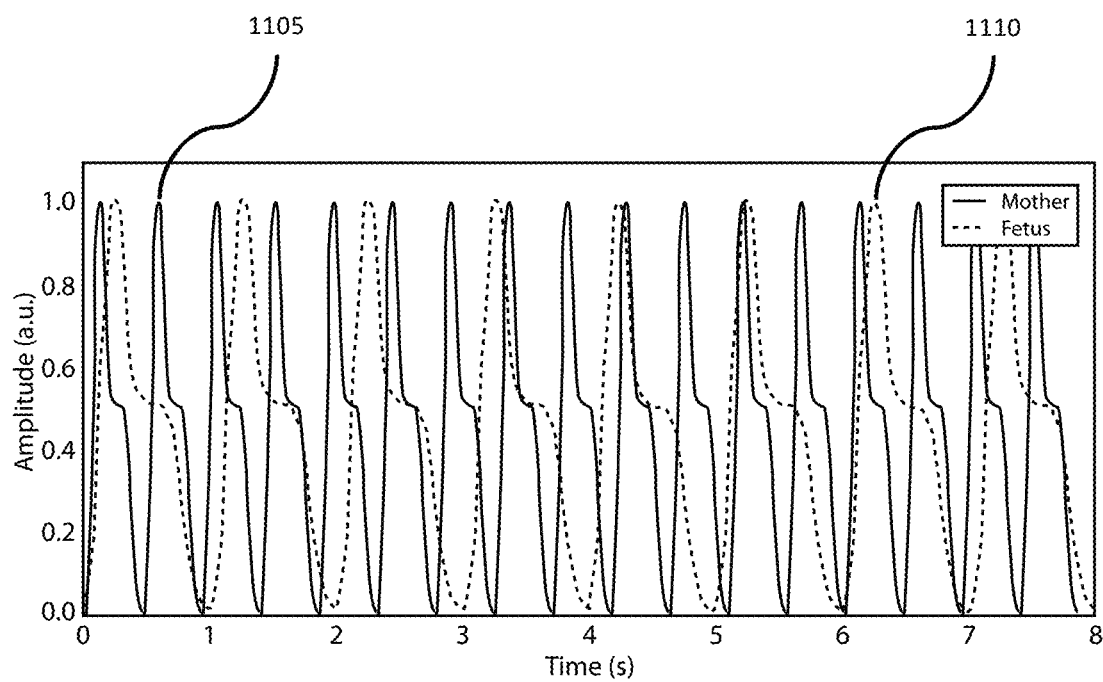
FIG. 11 provides a graph that plots a simulated fetal and maternal photoplethysmogram (PPG) over time in seconds, in accordance with some embodiments of the present invention.

In some embodiments, a photoplethysmogram (PPG) modulated signal may be integrated into one or more of the models generated and/or received in step 205 to simulate cardiac cycles for the pregnant mammal and/or fetus. The PPG modulated signal may have, for example, a variable 1% to 2% change in systolic blood volume for the pregnant mammal and/or fetus. FIG. 11 provides a graph 1100 that plots a simulated fetal and maternal PPG signals over time in seconds, wherein a PPG signal for the mother/pregnant mammal 1105 is shown in black and a PPG signal for the fetus 1110 is shown in grey. In some embodiments, noise and/or a confounding factor may be added to the PPG signal for the fetus 1110 and/or pregnant mammal 1105 as part of, for example, perturbation analysis using the model(s).

In step 210, one or more simulated optical inputs for the generation of simulated light transmission data as simulated light corresponding to the simulated optical inputs travels through the model of step 205 may be selected, received, and/or configured. Exemplary simulated optical inputs include, but are not limited to, simulated light wavelength, intensity, modulation of the light (e.g., a duration of successive light pulses), and/or a range of wavelengths. In some cases, the simulated optical inputs will be for the generation of simulated infra-red and/or near infra-red light.

Next, in step 215, a simulation using the model and simulated optical inputs of steps 205 and 210, respectively, may be run wherein simulated light is transmitted through the model and "detected" by a simulated photodetector. A result of execution of step 215 is the generation of a set of simulated light transmission data. In some cases, a set of simulated light transmission data may correspond to simulated light being transmitted through the model for a period of time (e.g., 15, 30, or 60 seconds; 1, 5, or 10 minutes). Step 215 may be executed a plurality (e.g., 50,000; 100,000; 500,000; 1,000,000; 5,000,000) of times thereby generating a plurality of sets of simulated light transmission data. The plurality of simulated light transmission data sets may then be stored in a database (step 220) like database 15 and/or 170. Simulated light transmission data sets may include a simulation of an electronic signal that may be "detected" by a photodetector responsively to detecting light (in this case, the simulated optical input) as it travels through the animal model.

In step 225, an oximetry value, which may correspond to a calculated fetal SpO2 value, for each set of simulated light transmission data may be determined and/or received. The oximetry value may be, for example, a maternal hemoglobin oxygen saturation level, a maternal tissue oxygenation level, a fetal hemoglobin oxygen saturation level, and/or a fetal tissue oxygenation level. When the oximetry values are hemoglobin oxygen saturation levels, the oximetry values may be determined via, for example, inputting the simulated light transmission data into the Beer Lambert Law or a modified version of the Beer Lambert Law as explained above using Equations 1 and 2. When the oximetry values are tissue oxygen saturation levels, the oximetry values may be determined via, for example, diffuse optical tomography (DOT) or another tissue oxygen saturation determination technique. Following step 225, the oximetry values and/or correlations between each set of simulated light transmission data and it's respective oximetry value may be stored in a database (step 230) like database 15 and/or 170.

Figure 3:
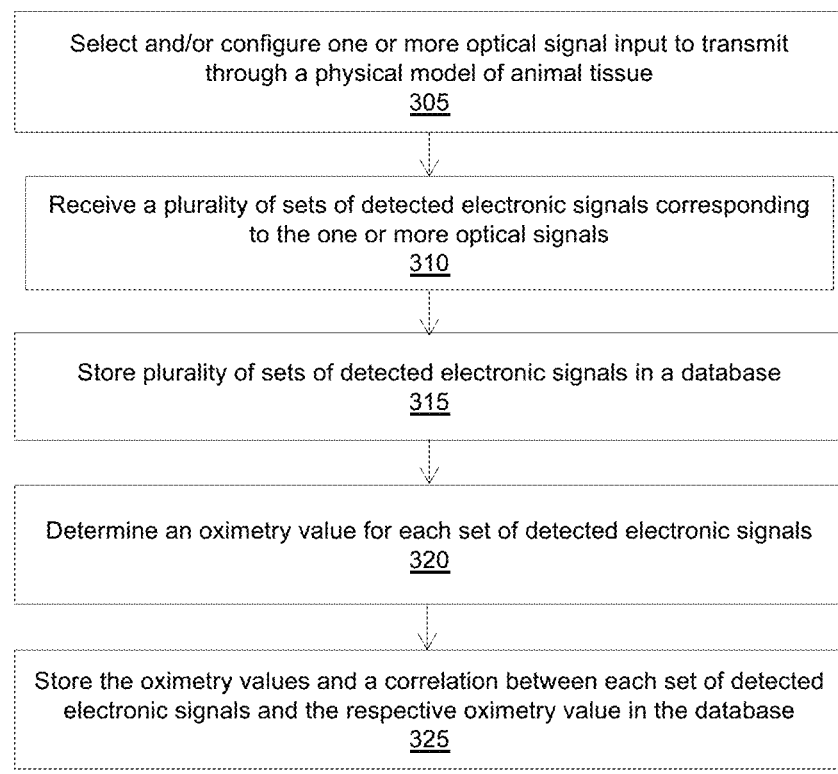
FIG. 3 is a flowchart showing an exemplary process for generating a plurality of sets of simulated light transmission data and corresponding oximetry values using light transmitted through a physical model of animal tissue, consistent with some embodiments of the present invention.

FIG. 3 is a flowchart showing an exemplary process 300 for generating a plurality of sets of simulated light transmission data and corresponding oximetry values using light transmitted through a physical model of animal tissue. Portions of process 300 may be executed by, for example, system 100, 10, and/or components thereof.

In step 305, one or more simulated optical inputs for the generation of one or more sets of simulated light transmission data as light travels through a physical model of tissue may be selected, received, and/or configured. The physical model of tissue may comprise one or more layers that have the same or different optical properties. The physical model may be made from for example, gels, aqueous solutions, and lipids. Exemplary optical inputs include, but are not limited to, light wavelength, intensity, modulation of the light (e.g., a duration of successive light pulses), and/or a range of wavelengths. In many cases, the optical inputs will be for the generation of infra-red and/or near infra-red light.

Next, in step 310, a plurality of sets of detected electronic signals corresponding to light generated using the optical inputs of step 305 that has passed through the physical model and been detected by a photodetector such as detector 160 may be received from the photodetector. In some cases, the detected electronic signals may correspond to light being transmitted through the physical model for a period of time (e.g., 15, 30, or 60 seconds; 1, 5, or 10 minutes). A result of execution of step 310 may be the generation of a set of simulated light transmission data. Step 310 may be executed a plurality (e.g., 50,000; 100,000; 500,000; 1,000,000; 5,000,000) of times thereby generating a plurality of sets of simulated light transmission data. The plurality of sets of detected electronic signals may then be stored in a database (step 315) like database 15 and/or 170.

In step 320, an oximetry value for each set of detected electronic signals may be determined and/or received. The oximetry value may be, for example, a maternal hemoglobin oxygen saturation level, a maternal tissue oxygenation level, a fetal hemoglobin oxygen saturation level, and/or a fetal tissue oxygenation level. When the oximetry values are hemoglobin oxygen saturation levels, the oximetry values may be determined via, for example, the Beer Lambert Law or a modified version of the Beer Lambert Law as explained above using Equations 1 and 2. When the oximetry values are tissue oxygen saturation levels, the oximetry values may be determined via, for example, diffuse optical tomography (DOT) or another tissue oxygen saturation determination technique. Following step 320, the oximetry values and/or correlations between each set of detected electronic signals (which may also be referred to herein as simulated light transmission data) and it's respective oximetry value may be stored in a database (step 325) like database 15 and/or 170.

Figure 4A:
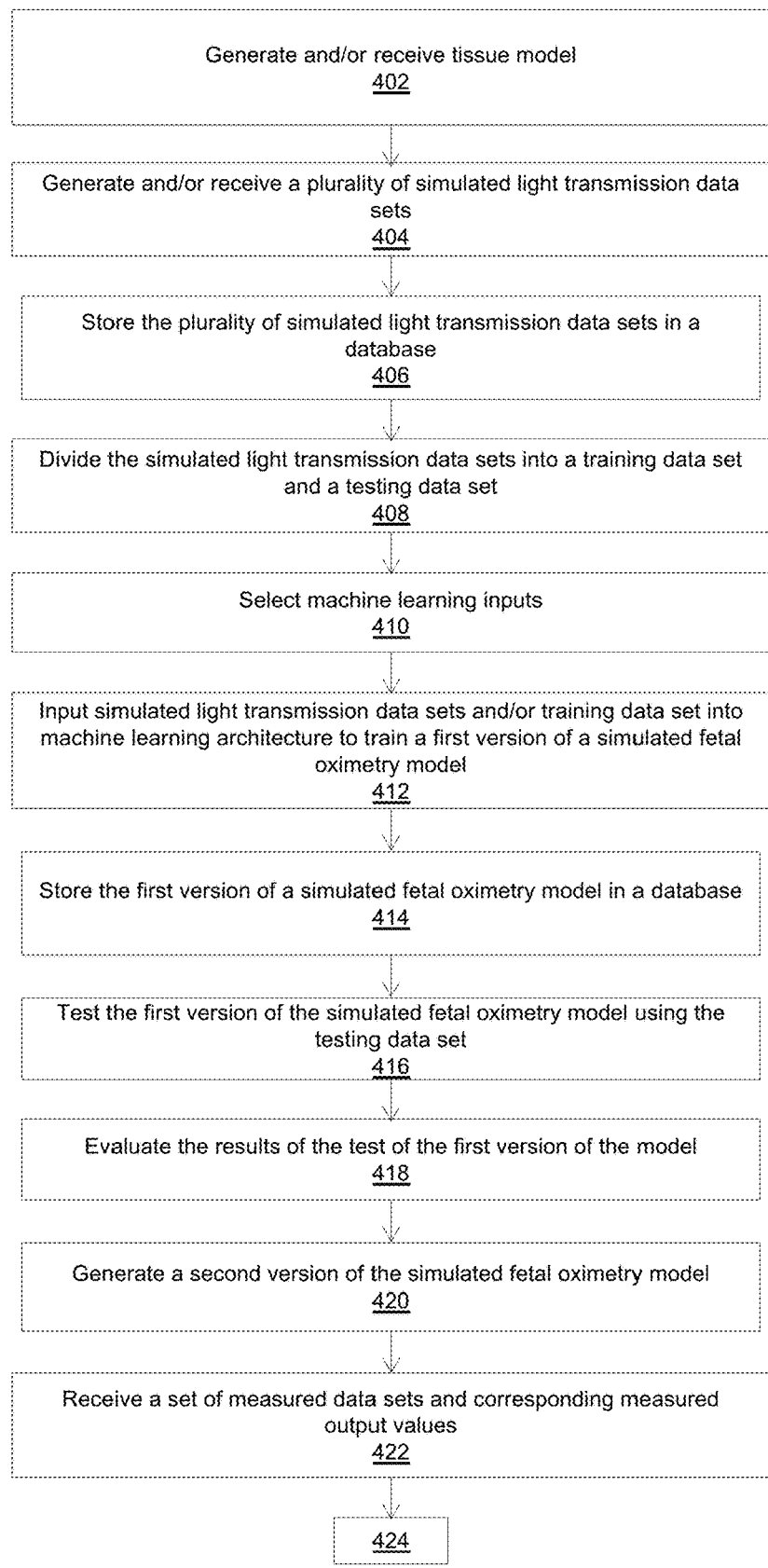
FIG. 4A is a flowchart illustrating a first part of an exemplary process for developing a model to compensate for the physio-optical influences of transabdominal fetal oximetry in order to accurately calculate fetal oxygen saturation in-utero, in accordance with some embodiments of the present invention.
Figure 4B:
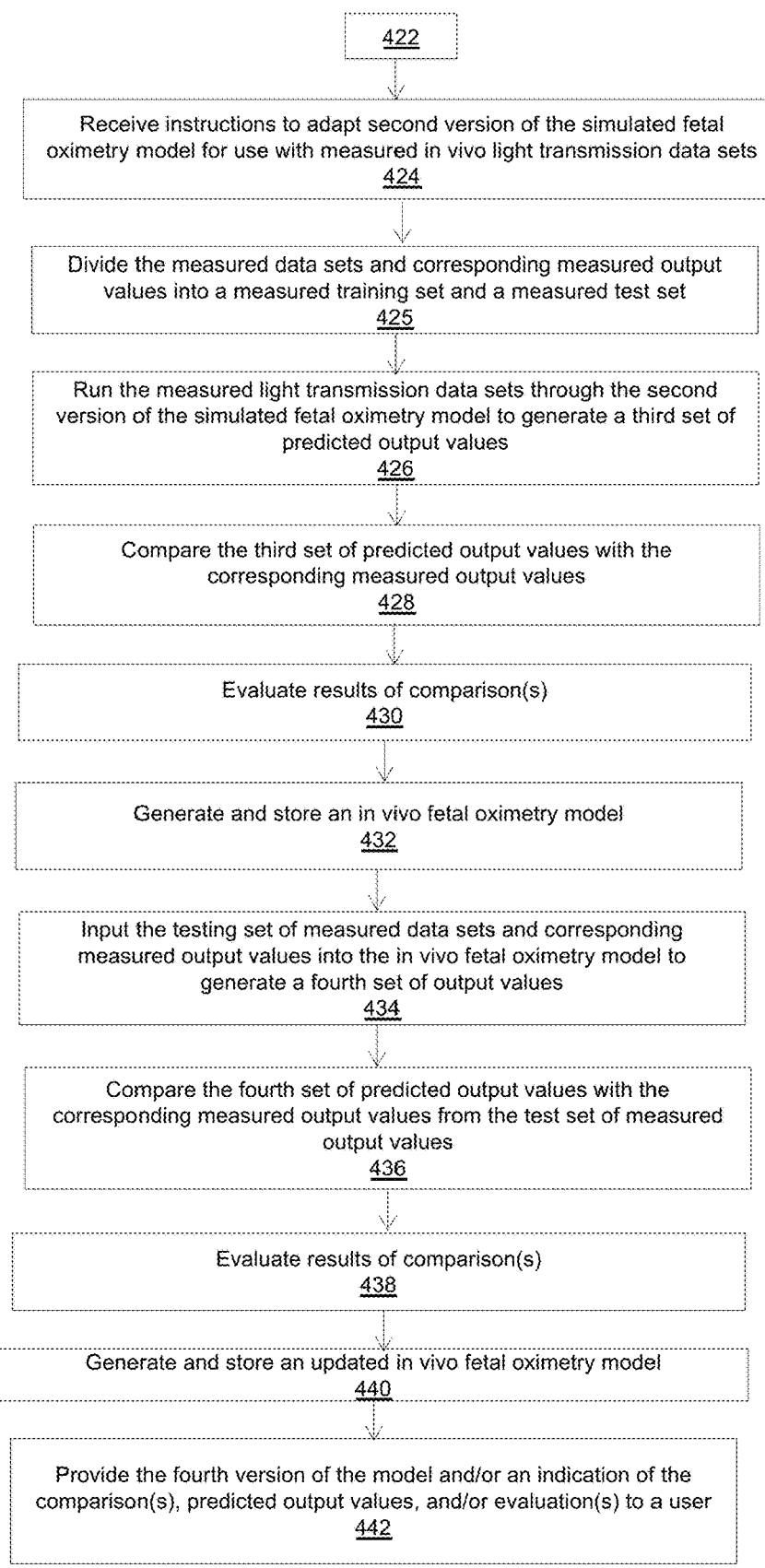
FIG. 4B is a flowchart illustrating a second part of the exemplary process of FIG. 4A, in accordance with some embodiments of the present invention.

FIGS. 4A and 4B provide a flowchart (over two pages) showing an exemplary process 400 for developing a model to accurately calculate oximetry values for a target tissue within a body, such as a fetus in-utero. Process 400 may be executed by, for example, system 100, 10, and/or components thereof.

Initially, in step 402, a tissue model may be received (e.g., following execution of process 200 and/or 300) and/or generated using, for example, a process similar to process 200 and/or 300. The tissue model may be a two and/or three-dimensional model of a portion of an animal (e.g., human) body with one or more layers of tissue. The modeled layer(s) of tissue may have different optical properties. An exemplary tissue model is provided by model 900 shown in FIG. 9, as discussed above. For the purposes of discussion, a layer of the tissue model may correspond to a model of abdominal tissue for a pregnant mammal and another layer may correspond to a model of fetal tissue but, it is noted that the models of other parts of the body that have two or more layers may also be received and/or generated in step 402. In some cases, execution of step 402 may also include receipt and/or selection of parameters or rules for the model such as the parameters showing in table 1000 of FIG. 10, discussed above.

In some embodiments, a photoplethysmogram (PPG) modulated signal may be integrated into one or more of the models generated in step 402 to simulate cardiac cycles for the pregnant mammal and/or fetus. The PPG modulated signal may have, for example, a variable 1% to 2% change in systolic blood volume for the pregnant mammal and fetus. FIG. 11 provides a graph 1100 that plots a simulated fetal and maternal PPG signals over time in seconds, wherein the PPG signal for the mother/pregnant mammal is shown in blue and the PPG signal for the fetus is shown in red. In some embodiments, noise and/or a confounding factor may be added to the PPG signal for the fetus and/or pregnant mammal as part of, for example, perturbation analysis using the models.

In step 404, a plurality (e.g., 500,000; 1,000,000; 5,000,000) of simulated light transmission data sets that simulate light traveling, over a period of time (e.g., 10 s, 30 s, 60 s, 5 minutes, etc.), through the models received and/or generated in step 402 and being detected by a detector like detector 160 may be generated and/or received. In some embodiments, execution of step 404 may include generation of one or more time series waveforms with variable fetal (100 to 240 BPM) and/or maternal (50 to 12 BPM) heartrates, amplitudes, and phases between them. Individual parameters used to generate each of the simulated light transmission data sets may be selected randomly, pseudo randomly, and/or systematically according to, for example, a physiologically appropriate distribution (e.g., likelihood of occurrence within a population) assigned to each parameter.

In some embodiments, execution of step 404 may include running a plurality (e.g., 50-500) of experiments and/or simulations with different inputs (e.g., fetal and maternal cross correlation with heartbeats, DC level, maternal SpO2, normalization ratios, fetal depth, and/or maternal optical scattering properties), different machine learning architectures. In some cases, different classifiers and/or loss functions may generate a large number (e.g., 2-5 million) of data sets from which fetal oximetry values (e.g., fetal SpO2, fetal tissue oxygen saturation, etc.) may be calculated. Additionally, or alternatively, execution of step 404 may include running a plurality (e.g., 50-500) of experiments and/or simulations with different inputs that pertain to features of equipment (e.g., detector sensitivity, lag times, light source characteristics, errors or noise that may be introduced into a signal when particular equipment is used, etc.) that may be used when taking in vivo light transmission and/or fetal oximetry measurements.

In some embodiments, execution of step 404 may include generating simulated light transmission data sets where the light transmission data is "received" from a plurality (e.g., 2, 4, 6, or 8) of different detectors and/or is transmitted by a plurality (e.g., 2, 4, 6, or 8) of sources. Additionally, or alternatively, the simulated detector signals may correspond to light of different wavelengths and/or from different types of light sources. Additionally, or alternatively, execution of step 404 may include generating desired features of the simulated light transmission data sets such as, for example, correlation amplitudes, DC levels, and/or fast Fourier transforms (FFTs). In some embodiments, execution of step 404 may include calculating one or more correlation amplitudes for the simulated light transmission data sets using, for example, time series data.

The received and/or generated simulated light transmission data sets may then be stored in a database like database 15 and/or 170 (step 406). Optionally, in step 408, the simulated light transmission data sets may then be divided into a training set (e.g., 60%, 70%, or 80% of the data sets) and a testing set (e.g., 40%, 30%, or 20% of the data sets).

Optionally, in step 410, inputs to the machine learning architecture and/or software program for determining fetal oximetry values may be selected. Exemplary inputs include, but are not limited to, fetal depth, fetal heart rate, maternal heart rate, equipment characteristics, background noise characteristics, maternal geometrical characteristics, maternal physiological characteristics, fetal geometrical characteristics, fetal physiological characteristics and/or maternal oximetry values (e.g., SpO2). In some embodiments, one or more inputs may be received from a component of system 100 such as ECG 175, Doppler/ultrasound probe 135, pulse oximetry probe 130, NIRS adult hemoglobin probe 125, and/or ventilator/ventilatory signal device. Input features may be normalized to standard mean and/or variance values, such as zero mean and unit variance, and, in some instances, may be combined into composite features that are then input into the machine learning architecture. In some cases, the machine learning architecture disclosed herein may be a deep learning network architecture that may include convolutional nets and engineered feature layers. Additionally, or alternatively, the machine learning architecture may be a neural network, an artificial neural network, a Bayesian network, and/or software or hardware that utilizes artificial intelligence. In some embodiments, execution of step 410 may include downsampling and/or activating one or convolutional layers of the machine learning architecture and/or a model (e.g., a simulated fetal oximetry model) generated by the machine learning architecture. In some cases, execution of step 410 may also include adding one or more engineered features, bias, and/or classifier layers to the machine learning architecture and/or a model (e.g., a simulated fetal oximetry model) generated by the machine learning architecture. Additionally or alternatively, models (e.g., simulated fetal oximetry models) generated by process 400 may include tree-based models or ensembles of layered and/or tree-based models. Additionally, or alternatively, models (e.g., simulated fetal oximetry models) generated by process 400 may incorporate K-fold cross-validation to, for example, generate the expected error, receiver operating characteristic (ROC), and/or area under the curve (AUC) values for the model.

In some embodiments, execution of step 410 may include selection of one or more types of outputs that may be incorporated into the machine learning architecture. Exemplary outputs include predicted fetal oximetry (e.g., SpO2 and/or fetal tissue oxygen saturation) values and a binary fetal hypoxia, fetal hypoxemia, fetal non-hypoxia, and/or fetal non-hypoxemia (e.g., fetal SpO2 above/below 30%) indication.

In step 412, the simulated light transmission data sets and/or training data set (when step 408 is executed) may be input into the machine learning architecture to generate and/or train a first version of a fetal oximetry model that may be configured to, for example, to predict a first set of outputs (e.g., fetal SpO2 values, fetal tissue oxygen saturation, and/or fetal hypoxemia or non-hypoxemia determinations). The first version of the simulated fetal oximetry model may include a plurality of layers and/or functions and, in some cases, may include one or more small layered network(s), sub-networks, and/or a Support Vector Machine. In some embodiments, execution of step 412 may include communication of the machine learning inputs and/or machine learning architecture to, for example, a machine learning computer platform and/or neural network such as a machine learning platform resident on/within cloud computing platform 11. In step 414, the first version of the simulated fetal oximetry model may be stored in a database such as database 15 and/or 170.

Optionally, in step 416, the first version of the simulated fetal oximetry model and/or first set of outputs may be tested using, for example, the testing data set from step 408. The results of the testing may then be evaluated (step 418) and used to modify the first version of the simulated fetal oximetry model thereby generating a second version of the simulated fetal oximetry model (step 420) via, for example, training and/or tuning the first version of the simulated fetal oximetry algorithm using the machine learning architecture. The second version of the simulated fetal oximetry model may be used to predict a second set of outputs. In some embodiments, the second version of the simulated fetal oximetry model may be similar, or identical to, the first version of the fetal oximetry model.

Then, in step 422, a set of measured, or actual, in vivo light transmission data sets and corresponding output data (e.g., fetal oximetry values such as fetal SpO2 and/or fetal tissue oxygenation saturation) may be received. The in vivo light transmission data sets may be received from a fetal oximetry probe such as fetal oximetry probe 115 and each corresponding output data/oximetry value may be calculated using a corresponding in vivo light transmission data set received in step 422. In one embodiment, the set of measured in vivo light transmission data sets and corresponding measured output data may include 200-10,000 datasets/output values. In the case of a pregnant human, the measured output data may be light transmission data sets taken over an interval of time (e.g., 30 or 60 seconds) and the measured, or actual, output values may be measured in vivo fetal oximetry values corresponding, in time, to when the light transmission data sets were measured. The In this example, measured in vivo fetal oximetry values may be within the range of, for example, of 10-70%. In some cases, the set of set of measured, or actual, output data may be converted into a format compatible with the predicted outputs so that a valid comparison between them may be made.

In step 424, instructions to adapt the first or second (when steps 416-420 are performed) version of the simulated fetal oximetry model for use in the generation of a first version of an in vivo fetal oximetry model. The first version of the in vivo fetal oximetry model may be generated by training, for example, the first/second version of the simulated fetal oximetry model using a plurality of measured in vivo light transmission data sets and corresponding measured in vivo fetal oximetry values.

Exemplary instructions received in step 424 include instructions to train, or update, only certain portions (e.g., layers, functions, networks, and/or sub-networks) of the first/second version of the simulated fetal oximetry model and fix, or hold constant, other portions of the fetal first/second version of the simulated fetal oximetry model as needed. Typically, the initial input layer or layers of the network would be fixed to preserve the features found in the simulations. Additionally, or alternatively, portions of the first/second version of the simulated fetal oximetry model that may remain fixed include portions of the first/second version of the simulated fetal oximetry model that are generally applicable to the in vivo fetal oximetry model such as, for example, layers pertaining to calibration factors, maternal and/or fetal physiology and/or geometry, and equipment parameters.

Optionally, in step 425, the measured in vivo light transmission data sets and corresponding output values (e.g., fetal oximetry values) may be divided into a measured training set and a measured testing set. In step 426, the in vivo light transmission data sets and corresponding output data (e.g., oximetry values) and/or the training set of in vivo light transmission data sets and corresponding output data (when step 424 is executed) may be input into an adapted (according to the instructions of step 424) version of the first/second version of the simulated fetal oximetry model so that one or more portions (e.g., layers or functions) of the first/second fetal oximetry model may be tuned or updated using the in vivo light transmission data and corresponding output values thereby generating an in vivo fetal oximetry model and, optionally, a third set of predicted output values generated by the in vivo fetal oximetry model.

In step 428, the third set of predicted output values may be compared with the corresponding measured output values to determine differences between them (step 428). Results of the comparison may then be evaluated (step 430) and used to update the in vivo fetal oximetry model (step 432). Execution of step 432 may also include storing the updated in vivo fetal oximetry model in a database such as the databases disclosed herein.

Optionally, when step 425 is performed, the testing set of measured light transmission data and corresponding output values may then be run through the in vivo fetal oximetry model to generate a fourth set of predicted output values (step 434). The fourth set of predicted output values may then be compared with the corresponding measured output values from the testing set of output values to determine differences between them (step 436). Results of the comparison may then be evaluated (step 438) and used to generate an updated in vivo fetal oximetry model to predict output values (step 440) using the machine learning architecture. The updated in vivo fetal oximetry model may also be stored in step 440. Then, the in vivo fetal oximetry model and/or an indication of the comparison(s), evaluation(s), and/or predicted output values may be provided to the user (step 442).

In some embodiments, process 400 and/or portions thereof may be repeated on a periodic, as-needed, and/or continuous basis to, for example, improve the accuracy of the predictions the model yields, perform perturbation analysis, and/or perform sensitivity analysis. When step 434 is not performed, process 400 may end at step 432.

FIG. 5 is a flowchart illustrating an exemplary process 500 for the generation of a simulated fetal oximetry model and/or a tuned simulated fetal oximetry model. Process 500 may be performed by, for example, any of the systems or system components disclosed herein and may use data, determinations, and/or models generated and/or used by any of the processes disclosed herein.

Initially, a plurality (e.g., 10,000-10 million) of sets of simulated light transmission data and corresponding oximetry values for each set of simulated light transmission data may be received by a processor or network of processors such as cloud computing platform 11 (step 505). Each set of the simulated light transmission data may have been generated by simulating a transmission of light of one more wavelengths and/or intensities through a model of animal tissue that may have been generated and/or received via, for example, execution of process 200 and/or 300. The oximetry values corresponding to each set of simulated light transmission data may have been generated via, for example, execution of process 200 and/or 300 and/or may be calculated as part of execution of step 505 using the simulated light transmission data. In some embodiments, the model of animal tissue may include at least two layers of animal tissue, one of which is fetal tissue (e.g., skin, bone, brain, blood, etc.). Optionally, in step 505, additional information regarding one or more of sets of simulated light transmission data and/or oximetry values may be received. The additional information may pertain to, for example, one or more of the following: fetal depth, source/detector separation distance, a thickness of maternal tissue, a type of maternal tissue, maternal and/or fetal skin color and/or melanin content, a thickness of fetal tissue, a type of fetal tissue, a type of light used, an intensity of light used, a light scattering property of layer of tissue in the model, a light absorption property of layer of tissue in the model, a fetal age, and/or calibration factor(s) associated with equipment used to obtain the simulated light transmission data, environmental conditions when the simulated light transmission data is collected.

Optionally, the plurality of sets of simulated light transmission data and corresponding fetal oximetry values may be divided into a training set of simulated data and a test set of simulated data (step 510). The plurality of sets of simulated light transmission data and corresponding fetal oximetry values may be divided along any appropriate ratio including, for example, 90:10 training/testing; 80:20 training/testing; or 70:30 training/testing. In some embodiments, execution of step 510 may be similar to execution of step 408.

In step 515, machine learning inputs for the generation of a simulated fetal oximetry model may be determined, set, and/or selected for input into a machine learning program and/or architecture such as herein described. In some embodiments, execution of step 515 may resemble execution of step 410. Then, in step 520, a simulated fetal oximetry model may be trained using all or most of the data (in all or most combinations) received in step 505 and/or the training set of data of step 510 when step 510 is executed. Step 520 may be executed via, for example, inputting the simulated light transmission data, simulated detected electronic signals, corresponding oximetry values and/or addition information and/or a training set thereof (when step 510 is executed) into the machine learning architecture once it is set up with the machine learning inputs of step 515. The simulated fetal oximetry model may be configured to receive a plurality of sets of simulated light transmission data included in the training set of simulated data and determine an oximetry value a fetus for each set of simulated light transmission data included in the training set of simulated data. This determined oximetry value may then be compared with the corresponding oximetry value received in step 505 to determine any differences therebetween. Results of this comparison may be used to iteratively update/train the simulated fetal oximetry model during execution of step 520. Training of the simulated fetal oximetry model may be complete (step 525) when, for example, a number or proportion (e.g., 60-99%) of the oximetry values calculated by the simulated fetal oximetry model using one or more simulated light transmission data sets received in step 505 are sufficiently close to (e.g., within a standard of deviation, within 0.5 standards of deviation, within 0.1 standards of deviation, and/or within 60-99% of the associated oximetry value) of the oximetry values associated each of the respective simulated light transmission data sets. When the training of the simulated fetal oximetry model is not complete (step 525), step 520 may be repeated. When step 510 is not executed, process 500 may end following a determination that the training of the simulated fetal oximetry model in step 525 is complete.

In some embodiments, the simulated fetal oximetry model includes a plurality of layers, factors, calibrations, and/or functions (referred to herein collectively as "layers") that are used to calculate oximetry values using the simulated light transmission data. Layers may include functions that account for and/or factor in, for example, fetal depth, source/detector separation distance, a thickness of maternal tissue, a type of maternal tissue, maternal and/or fetal skin color and/or melanin content, a thickness of fetal tissue, a type of fetal tissue, a type of light used, an intensity of light used, a fetal age, and/or calibration factor(s) associated with equipment that may be used in clinical applications to obtain in vivo measurements of light transmission data, environmental conditions that may be present during clinical applications when in vivo measurements of light transmission data is collected.

When the training of the simulated fetal oximetry model is complete (step 525), the simulated fetal oximetry model may be tested with the testing set of simulated data (step 530). In some embodiments, execution of step 530 may be similar to execution of step 416. Results of the testing of the simulated fetal oximetry model may then be evaluated (step 535) to, for example, determine how accurately the simulated fetal oximetry model calculated oximetry values. In some cases, the testing of step 530 may be iterative. When the testing of the simulated fetal oximetry model is complete (step 540), the simulated fetal oximetry model may be tuned responsively to one or more results of the testing and/or evaluation of the tests (step 545) thereby generating a tuned simulated fetal oximetry model and process 500 may end. When the testing of the simulated fetal oximetry model is not complete (step 540), process 500 may proceed to step 530.

Figure 6:
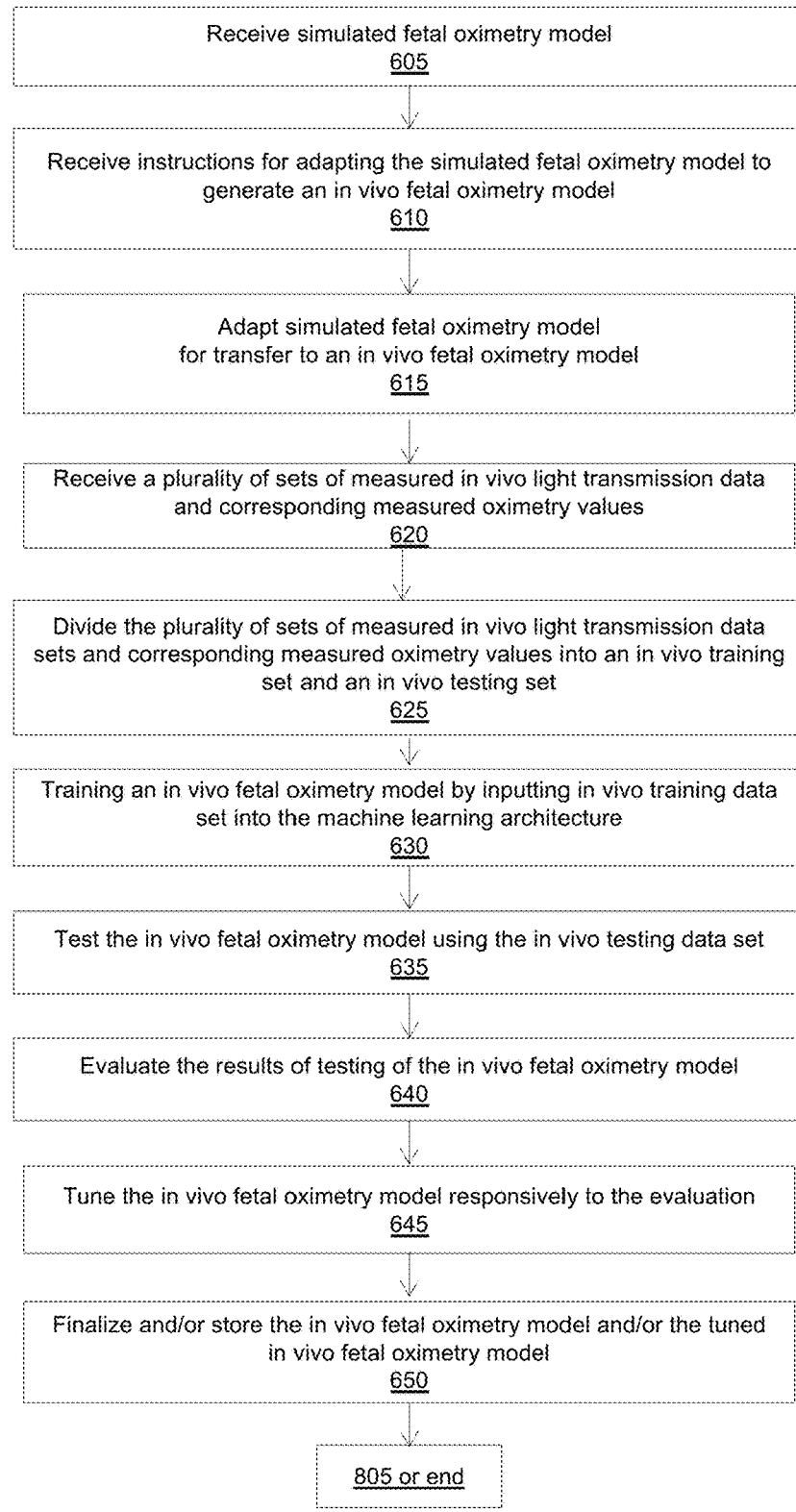
FIG. 6 is a flowchart illustrating a process for the generation of a tuned in vivo fetal oximetry model, consistent with some embodiments of the present invention.

FIG. 6 is a flowchart illustrating an exemplary process 600 for the generation of an in vivo fetal oximetry model and/or a tuned in vivo fetal oximetry model. Process 600 may be performed by, for example, any of the systems or system components disclosed herein and may use data, determinations, and/or models generated and/or used by any of the processes disclosed herein. In some embodiments, process 600 may be performed subsequently to performance of process 500 and, on occasion, may be executed by the same systems and/or processors.

In step 605, a tuned simulated fetal oximetry model, such as the tuned simulated fetal oximetry model generated by process 500, may be received by, for example, a processor or network of processors such as cloud computing platform 11. Additionally, or alternatively, when, for example, steps 530-545 of process 500 are executed, a tuned simulated fetal oximetry model may be received in step 605. For ease of discussion, the following discussion of process 600 will refer to a "simulated fetal oximetry model" as referring to both the simulated fetal oximetry model (of, for example, step 525) and the tuned simulated fetal oximetry model (of, for example, step 545).

Instructions to adapt the simulated fetal oximetry model for transfer to an in vivo fetal oximetry model may then be received (step 610). In some cases, the instructions to adapt the simulated fetal oximetry model for transfer to an in vivo fetal oximetry model may include instructions to fix one or more layers, or functions, of the simulated fetal oximetry model that may be generally applicable to the in vivo fetal oximetry model. Exemplary layers and/or functions of the tuned simulated fetal oximetry model that may be fixed include, but are not limited to, how one or more of a source/detector distance, a wavelength of light, a fetal depth, maternal skin color, fetal skin color, maternal tissue composition, fetal tissue composition and/or a calibration factor impact (e.g., weights in the model), an oximetry calculation.

Then, the tuned simulated fetal oximetry model may be adapted for transfer to an in vivo fetal oximetry model responsively to the instructions (step 615). In some cases, the adapting of step 615 may include determining, setting, and/or selecting one or more machine learning inputs for a machine learning architecture for the generation of an in vivo fetal oximetry model. Additionally, or alternatively, the adapting of step 615 may include fixing one or more layers, or functions, of the tuned simulated fetal oximetry model so that it remains fixed during the in vivo fetal oximetry model training process (step 630, which is discussed below).

In step 620, a plurality (e.g., 1,000-10 million) of sets of in vivo light transmission data and corresponding fetal oximetry values for each set of in vivo light transmission may be received. The plurality of sets of in vivo light transmission data may be received from, for example, a fetal oximetry probe like fetal oximetry probe 115 and the corresponding fetal oximetry values may be calculated using, for example, Equations 1 and 2 as discussed herein.

Optionally, in step 625, the plurality of sets of in vivo light transmission data and corresponding fetal oximetry values may then be divided into a training set of in vivo data and a test set of in vivo data. The plurality of sets of in vivo light transmission data and corresponding fetal oximetry values may be divided along any appropriate ratio including, for example, 90:10 training/testing; 80:20 training/testing; or 70:30 training/testing. In some embodiments, execution of step 625 may have one or more similarities with execution of step 408 and/or 510.

In step 630, an in vivo fetal oximetry model may be trained using the training set of in vivo data and the adapted simulated fetal oximetry model. Step 630 may be executed via, for example, inputting the training set of in vivo data into the machine learning architecture once it is set up with the adapted simulated fetal oximetry model of step 615. In some embodiments, the in vivo fetal oximetry model may be configured to receive a plurality of sets of in vivo light transmission data included in the plurality of sets of measured in vivo data and/or training set of in vivo data and determine an oximetry value of a fetus for each respective set of in vivo light transmission data. This determined oximetry value may then be compared with the oximetry value associated with the in vivo light transmission data to determine any differences therebetween. These differences may be used to, for example, iteratively update/train the in vivo fetal oximetry model during execution of step 630. Training of the in vivo fetal oximetry model may be complete when, for example, a number or proportion (e.g., 60-99%) of the oximetry values calculated by the in vivo fetal oximetry model using one or more in vivo light transmission data sets received in step 620 are sufficiently close to (e.g., within a standard of deviation, within 0.5 standards of deviation, within 0.1 standards of deviation, and/or within 60-99% of the associated oximetry value) to the oximetry values associated with each of the respective in vivo transmitted light data sets. When the training of the in vivo fetal oximetry model is not complete, step 630 may be repeated and/or may continue to be executed.

In some embodiments, the in vivo fetal oximetry model includes a plurality of layers, factors, calibrations, and/or functions (referred to herein collectively as "layers") that are used to calculate oximetry values using the in vivo light transmission data. Exemplary layers include functions that factor in, account for, and/or are associated with, for example, fetal depth, source/detector separation distance, a thickness of maternal tissue, a type of maternal tissue, maternal and/or fetal skin color and/or melanin content, a thickness of fetal tissue, a type of fetal tissue, a type of light used, an intensity of light used, a fetal age, and/or calibration factor(s) associated with equipment used to obtain the in vivo light transmission data, environmental conditions when the in vivo light transmission data is collected.

When the training of the in vivo fetal oximetry model is complete, process 600 may optionally proceed to step 650. Alternatively, and optionally, when the training of the in vivo fetal oximetry model is complete, the in vivo fetal oximetry model may be tested with the testing set of in vivo data (step 635). Optionally, results of the testing of the in vivo fetal oximetry model may then be evaluated (step 640) to, for example, determine how accurate the in vivo fetal oximetry model calculated oximetry values are. In some cases, the testing of step 635 may be iterative. When the testing of the in vivo fetal oximetry model is complete, the in vivo fetal oximetry model may be tuned and/or updated responsively to one or more results of the testing and/or evaluation of the tests (step 645) thereby generating a tuned in vivo fetal oximetry model. The tuned in vivo fetal oximetry model may then be finalized and/or stored and process 600 may end.

FIG. 7 is a flowchart illustrating an exemplary process 700 for the generation of an in vivo fetal oximetry model. Process 700 may be performed by, for example, any of the systems or system components disclosed herein and may use data, determinations, and/or models generated and/or used by any of the processes disclosed herein.

Initially, a plurality (e.g., 100,000-10 million) of sets of simulated light transmission data and corresponding oximetry values for each set of simulated light transmission data may be received by a processor or network of processors such as cloud computing platform 11 (step 705). Each set of the simulated light transmission data may have been generated by simulating a transmission of light of one more wavelengths and/or intensities through a model of animal tissue that may have been generated and/or received via, for example, execution of process 200 and/or 300. The simulated light transmission data sets may resemble those received in, for example, step 404. In some embodiments, the oximetry values corresponding to each set of simulated light transmission data may have been generated via, for example, execution of process 200 and/or 300 and/or may be calculated as part of execution of step 705 using the simulated light transmission data. In some embodiments, the model of animal tissue may include at least two layers of animal tissue, one of which is fetal tissue (e.g., skin, bone, brain, blood, etc.). On some occasions, execution of step 705 may resemble execution of step 505.

In step 710, machine learning inputs for the generation of a simulated fetal oximetry model may be determined, set, and/or selected for input into a machine learning program and/or architecture such as TensorFlow. In some embodiments, execution of step 710 may resemble execution of step 410 and/or 515. Then, in step 715, a simulated fetal oximetry model may be trained using the simulated light transmission data sets and corresponding oximetry values. Step 715 may be executed via, for example, inputting the simulated light transmission data and corresponding oximetry values into the machine learning architecture once it is set up with the machine learning inputs of step 710. At times, execution of step 715 may resemble execution of step 520.

The simulated fetal oximetry model may be trained and/or configured to receive a plurality of sets of simulated light transmission data and determine an oximetry value for a fetus that may be associated with each set of simulated light transmission data. This determined oximetry value may then be compared with the oximetry value associated with respective sets of simulated light transmission data received in step 705 to determine any differences therebetween. Results of this comparison may be used to iteratively update/train the simulated fetal oximetry model during execution of step 715. Training of the simulated fetal oximetry model may be complete (step 720) when, for example, a number or proportion (e.g., 60-99%) of the oximetry values calculated by the simulated fetal oximetry model using one or more simulated light transmission data sets received in step 705 are sufficiently close to (e.g., within a standard of deviation, within 0.5 standards of deviation, within 0.1 standards of deviation, and/or within 60-99% of the associated oximetry value) of the oximetry values associated each of the respective simulated light transmission data sets. When the training of the simulated fetal oximetry model is not complete (step 720), step 715 may be iteratively repeated. In some embodiments, execution of step 720 may resemble execution of step 525.

In some embodiments, the simulated fetal oximetry model includes a plurality of layers, factors, calibrations, and/or functions (referred to herein collectively as "layers") that are used to calculate oximetry values using the simulated light transmission data. Layers may include, for example, functions that account for and/or factor in, for example, fetal depth, source/detector separation distance, a thickness of maternal tissue, a type of maternal tissue, maternal and/or fetal skin color and/or melanin content, a thickness of fetal tissue, a type of fetal tissue, a type of light used, an intensity of light used, a fetal age, and/or calibration factor(s) associated with equipment that may be used in clinical applications to obtain in vivo measurements of light transmission data, environmental conditions that may be present during clinical applications when in vivo measurements of light transmission data is collected. When the training of the simulated fetal oximetry model is complete (step 720), it may be stored in a database like database 15 and/or 170 (step 725).

In step 730, instructions to adapt the simulated fetal oximetry model for transfer to an in vivo fetal oximetry model may then be received. In some cases, the instructions to adapt the simulated fetal oximetry model for transfer to an in vivo fetal oximetry model may include instructions to fix one or more layers, or functions, of the simulated fetal oximetry model that may be generally applicable to the in vivo fetal oximetry model so that these fixed layers/functions do not change during the training process. Exemplary layers and/or functions of the simulated fetal oximetry model that may be fixed include, but are not limited to, how one or more of a source/detector distance, a wavelength of light, a fetal depth, maternal skin color, fetal skin color, maternal tissue composition, fetal tissue composition and/or a calibration factor impact (e.g., weights in the model), an oximetry calculation. In some embodiments, execution of step 730 may resemble execution of step 424 and/or 610.

Then, the simulated fetal oximetry model may be adapted for transfer to an in vivo fetal oximetry model responsively to the instructions (step 735). In some cases, the adapting of step 735 may include determining, setting, and/or selecting one or more machine learning inputs for a machine learning architecture for the generation of an in vivo fetal oximetry model. Additionally, or alternatively, the adapting of step 735 may include fixing one or more layers, or functions, of the simulated fetal oximetry model so that it remains fixed during the in vivo fetal oximetry model training process (step 745, which is discussed below).

In step 740, a plurality (e.g., 1,000-10 million) of sets of in vivo light transmission data and corresponding fetal oximetry values for each set of in vivo light transmission may be received. The plurality of sets of in vivo light transmission data may be received from, for example, a fetal oximetry probe like fetal oximetry probe 115 and the corresponding fetal oximetry values may be calculated using, for example, Equations 1 and 2 as discussed herein. Then, in step 745, an in vivo fetal oximetry model may be generated and/or trained using the in vivo data and the adapted simulated fetal oximetry model of step 735. Step 745 may be executed via, for example, inputting a plurality of sets of in vivo data into the machine learning architecture once it is set up with the adapted simulated fetal oximetry model of step 735. The in vivo fetal oximetry model may be configured to receive a plurality of sets of in vivo light transmission data and determine an oximetry value of a fetus for each set of in vivo light transmission data included in the training set of in vivo data. This determined oximetry value may then be compared with the oximetry value associated with a respective set of in vivo light transmission data that may be received in step 740 to determine any differences therebetween. These differences may be used to, for example, iteratively update/train the in vivo fetal oximetry model during execution of step 745. Training of the in vivo fetal oximetry model may be complete (step 750) when, for example, a number or proportion (e.g., 60-99%) of the oximetry values calculated by the in vivo fetal oximetry model using one or more in vivo light transmission data sets received in step 740 are sufficiently close to (e.g., within a standard of deviation, within 0.5 standards of deviation, within 0.1 standards of deviation, and/or within 60-99% of the associated oximetry value) to the oximetry values associated with each of the respective in vivo transmitted light data sets.

In some embodiments, the in vivo fetal oximetry model includes a plurality of layers, factors, calibrations, and/or functions (referred to herein collectively as "layers") that are used to calculate oximetry values using the in vivo light transmission data. Exemplary layers include functions that factor in and/or account for associated with, for example, fetal depth, source/detector separation distance, a thickness of maternal tissue, a type of maternal tissue, maternal and/or fetal skin color and/or melanin content, a thickness of fetal tissue, a type of fetal tissue, a type of light used, an intensity of light used, a fetal age, and/or calibration factor(s) associated with equipment used to obtain the in vivo light transmission data, environmental conditions when the in vivo light transmission data is collected.

When the training of the in vivo fetal oximetry model is not complete, (step 745) may be repeated and/or may continue to be iteratively executed. When the training of the in vivo fetal oximetry model is complete (step 745), the vivo fetal oximetry model may then be finalized and stored (step 755) and process 700 may end or proceed to step 805 of process 800 discussed below.

Figure 8:
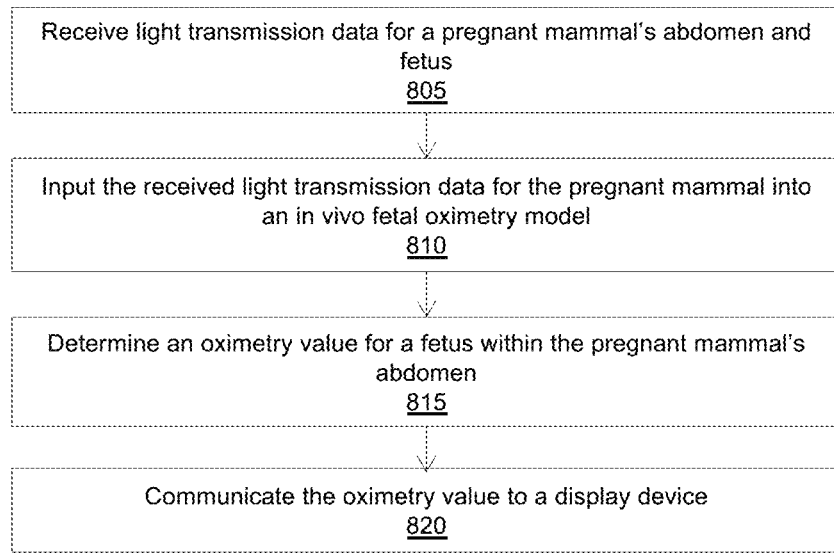
FIG. 8 is a flowchart illustrating a process for the determination of an oximetry value for a fetus using an in vivo fetal oximetry model, consistent with some embodiments of the present invention.

FIG. 8 is a flowchart illustrating an exemplary process 800 for the determination of a fetal oximetry value for a fetus using an in vivo fetal oximetry model that may be generated via, for example, execution of process 600 and/or 700. Process 800 may be performed by, for example, any of the systems or system components disclosed herein.

Initially, in step 805, light transmission data for a pregnant mammal's abdomen and fetus may be received from, for example, a photodetector like detector 160 and/or a probe like fetal hemoglobin probe 115. The light may be transmitted from a light source, through the pregnant mammal's abdomen and fetus and/or backscattered from the abdominal/fetal tissue, and detected by the photodetector. The light transmission data received in step 805 may then be put into and/or processed by the in vivo fetal oximetry model (which may be the finalized in vivo fetal oximetry model of step 650 in step 810. In some embodiments, the light transmission data received in step 805 may be pre-processed prior to execution of step 810. The pre-processing may include, for example, filtering with, for example, a Kalman or bandpass filter, application of a noise reduction model, removal of a portion of the light transmission data that is incident only the pregnant mammal (i.e., not incident on the fetus), and/or isolation of a portion of the light incident on the fetus from the received light transmission data. On some occasions, removal of a portion of the light transmission data that is incident only the pregnant mammal (i.e., not incident on the fetus), and/or isolation of a portion of the light incident on the fetus from the received light transmission data may be accomplished by, for example, receiving a maternal heartrate signal, using the maternal heart rate signal to identify the portion of the light transmission data contributed by the pregnant mammal and then subtracting the portion of the light transmission data contributed by the pregnant mammal from the light transmission data. Additionally, or alternatively, isolation of the fetal portion of the light transmission data may be accomplished by, for example, receiving a fetal heartrate signal, using the fetal heart rate signal to identify the portion of the light transmission data contributed by the fetus and then subtracting the remainder of light transmission data and/or amplifying the portion of the light transmission data contributed by the fetus. Additionally, or alternatively, isolation of the fetal portion of the light transmission data may include determining a fetal position and/or fetal depth and then In step 815, an oximetry value for the fetus within the pregnant mammal's abdomen may be determined and/or output by the in vivo fetal oximetry model. The oximetry value may be, for example, a fetal hemoglobin oxygen saturation level, a fetal tissue oxygen saturation level, an indication of fetal hypoxia, an indication of fetal hypoxemia, and/or an alert condition indicating that a fetal oximetry value indicates the fetus may be in distress. The oximetry value may then be communicated to a display device like display device 14 and/or 155 for display to a user such as a clinician and/or the pregnant mammal.

We claim:

1. A method comprising:
    determining information regarding a blood oxygen value of a fetus, the determining comprising:
        obtaining at least one signal indicating light detected from a pregnant mammal's abdomen and/or a fetus disposed in the pregnant mammal's abdomen following application of light to the pregnant mammal's abdomen; and
        analyzing the at least one signal using at least one trained model trained, using both results of simulations of light applications to pregnant mammal abdomens and results of light applications to pregnant mammal abdomens, to determine blood oxygen information used to determine the information regarding the blood oxygen value of the fetus.

2. The method of claim 1, wherein the information regarding the blood oxygen value of the fetus is a level of fetal hemoglobin oxygen saturation.

3. The method of claim 1, wherein the information regarding the blood oxygen value of the fetus is a level of fetal tissue oxygen saturation.

4. The method of claim 1, further comprising:
determining whether the fetus has fetal hypoxia or fetal hypoxemia using the blood oxygen value; and
providing an indication of a determination that the fetus has fetal hypoxia or fetal hypoxemia to a display device.

5. The method of claim 1, wherein the at least one trained model is further trained using results of simulations of light applications to pregnant mammal abdomens that incorporate optical properties of the respective pregnant mammal abdomens, the method further comprising:
receiving an optical property of the pregnant mammal corresponding to the at least one signal, wherein the analysis of the at least one signal is responsive to the received optical property.

6. The method of claim 5, wherein the optical property is at least one of a light scattering coefficient and a light absorption coefficient.

7. The method of claim 1, wherein the at least one trained model is further trained using results of simulations of light applications to pregnant mammal abdomens that incorporate at least one of skin color of the respective pregnant mammal abdomens and skin melanin content of the respective pregnant mammal abdomens, the method further comprising:
receiving at least one of skin color and skin melanin content for the pregnant mammal corresponding to the at least one signal, wherein the analysis of the at least one signal is responsive to the received at least one of skin color and skin melanin content for the pregnant mammal.

8. The method of claim 1, wherein the at least one trained model is further trained using results of simulations of light applications to pregnant mammal abdomens that incorporate additional information regarding the respective pregnant mammal abdomens and/or fetuses, the method further comprising:
receiving additional information regarding the pregnant mammal and/or fetus corresponding to the at least one signal, wherein the analysis of the at least one signal is responsive to the received additional information.

9. The method of claim 1, wherein the at least one trained model is further trained using results of simulations of light applications to pregnant mammal abdomens that incorporate blood oxygen levels of the respective pregnant mammal abdomens, the method further comprising:
receiving a blood oxygen level of the pregnant mammal corresponding to the at least one signal, wherein the analysis of the at least one signal is responsive to the received blood oxygen level of the pregnant mammal.

10. The method of claim 1, wherein the at least one trained model is further trained using results of simulations of light applications to pregnant mammal abdomens that incorporate geometrical properties of the respective pregnant mammal abdomens, the method further comprising:
receiving an geometrical property of the pregnant mammal corresponding to the at least one signal, wherein the analysis of the at least one signal is responsive to the received anatomical property.

11. A method comprising:
determining information regarding a blood oxygen value of a patient, the determining comprising:
obtaining at least one signal indicating light detected from the patient following application of light to the patient; and
analyzing the at least one signal using at least one trained model trained, using both results of simulations of light applications to subjects and results of light applications to subjects, to determine blood oxygen information.

12. The method of claim 11, wherein the information regarding the blood oxygen value of the patient is a level of hemoglobin oxygen saturation for the patient.

13. The method of claim 11, wherein the information regarding the blood oxygen value of the patient is a level of tissue oxygen saturation for the patient.

14. The method of claim 11, further comprising:
determining whether the patient has hypoxia or hypoxemia using the blood oxygen value; and
providing an indication of a determination that the patient has hypoxia or hypoxemia to a display device.

15. The method of claim 11, wherein the at least one trained model is further trained using results of simulations of light applications to subjects that incorporate optical properties of the respective subjects, the method further comprising:
receiving an optical property of the patient corresponding to the at least one signal, wherein the analysis of the at least one signal is responsive to the received optical property.

16. The method of claim 15, wherein the optical property is at least one of a light scattering coefficient and a light absorption coefficient.

17. The method of claim 11, wherein the at least one trained model is further trained using results of simulations of light applications to subjects that incorporate at least one of skin color of the respective subject and skin melanin content of the respective subjects, the method further comprising:
receiving at least one of skin color and skin melanin content for the patient corresponding to the at least one signal, wherein the analysis of the at least one signal is responsive to the received at least one of skin color and skin melanin content for the patient.

18. The method of claim 11, wherein the at least one trained model is further trained using results of simulations of light applications to subjects that incorporate additional information regarding the respective subjects, the method further comprising:
receiving additional information regarding the patient corresponding to the at least one signal, wherein the analysis of the at least one signal is responsive to the received additional information.

19. The method of claim 11, wherein the at least one trained model is further trained using results of simulations of light applications to subjects that incorporate anatomical properties of the respective subjects, the method further comprising:
receiving an anatomical property of the patient corresponding to the at least one signal, wherein the analysis of the at least one signal is responsive to the received anatomical property.

20. A system comprising:
a processor configured to execute a set of instructions stored on a memory; and the memory communicatively coupled to the processor, the memory storing the set of instructions, which when executed by the processor cause the processor to:

determine information regarding a blood oxygen value of a fetus, the determining comprising:

obtaining at least one signal indicating light detected from a pregnant mammal's abdomen and/or a fetus disposed in the pregnant mammal's abdomen following application of light to the pregnant mammal's abdomen; and analyzing the at least one signal using at least one trained model trained, using both results of simulations of light applications to pregnant mammal abdomens and results of light applications to pregnant mammal abdomens, to determine blood oxygen information used to determine the information regarding the blood oxygen value of the fetus.

21. A system comprising:

a processor configured to execute a set of instructions stored on a memory; and the memory communicatively coupled to the processor, the memory storing the set of instructions, which when executed by the processor cause the processor to:

determine information regarding a blood oxygen value of a patient, the determining comprising:

obtaining at least one signal indicating light detected from the patient following application of light to the patient; and analyzing the at least one signal using at least one trained model trained, using both results of simulations of light applications to subjects and results of light applications to subjects, to determine blood oxygen information.

\* \* \* \* \*